(12) United States Patent
Serhan et al.

(10) Patent No.: US 7,344,539 B2
(45) Date of Patent: Mar. 18, 2008

(54) INTERVERTEBRAL CONNECTION SYSTEM

(75) Inventors: Hassan A Serhan, S. Easton, MA (US);
Michael A Slivka, Taunton, MA (US);
Christopher T Fair, Barrington, RI (US)

(73) Assignee: Depuy Acromed, Inc., Raynham, MA (US)

( * ) Notice: Subject to any disclaimer, the term of this patent is extended or adjusted under 35 U.S.C. 154(b) by 421 days.

(21) Appl. No.: 09/822,126

(22) Filed: Mar. 30, 2001

(65) Prior Publication Data

US 2002/0143329 A1    Oct. 3, 2002

(51) Int. Cl.
*A61B 17/56*   (2006.01)
*A61F 2/08*   (2006.01)
(52) U.S. Cl. ..................... 606/72; 623/13.11
(58) Field of Classification Search ............... 606/72, 606/61; 623/13.14, 13.18, 13.11, 13.12, 623/FOR. 109, 13.19
See application file for complete search history.

(56) References Cited

U.S. PATENT DOCUMENTS

| | | | |
|---|---|---|---|
| 3,463,158 A | 8/1969 | Schmitt et al. | |
| 3,513,484 A * | 5/1970 | Hausner | 623/13 |
| 3,710,789 A | 1/1973 | Ersek | |
| 3,988,783 A | 11/1976 | Treace | |
| 4,127,902 A * | 12/1978 | Hosy | 623/13 |
| 4,255,820 A * | 3/1981 | Rothermel et al. | 623/13 |
| 4,401,112 A | 8/1983 | Rezaian | |
| 4,403,606 A | 9/1983 | Woo et al. | |
| 4,409,968 A | 10/1983 | Drummond | |
| 4,411,259 A | 10/1983 | Drummond | |
| 4,570,623 A | 2/1986 | Ellison et al. | |
| 4,570,624 A | 2/1986 | Wu | |
| 4,610,688 A | 9/1986 | Silvestrini et al. | |
| 4,641,636 A | 2/1987 | Cotrel | |
| 4,665,951 A | 5/1987 | Ellis | |
| 4,728,329 A | 3/1988 | Mansat | |
| 4,743,260 A | 5/1988 | Burton | |
| 4,755,183 A | 7/1988 | Kenna | |
| 4,772,287 A | 9/1988 | Ray et al. | |
| 4,773,406 A | 9/1988 | Spector et al. | |
| 4,790,303 A | 12/1988 | Steffee | |
| 4,792,336 A | 12/1988 | Hlavacek et al. | |
| 4,815,453 A | 3/1989 | Cotrel | |
| 4,820,305 A | 4/1989 | Harms et al. | |
| 4,828,562 A | 5/1989 | Kenna | |
| 4,834,755 A | 5/1989 | Silvestrini et al. | |
| 4,883,486 A | 11/1989 | Kapadia et al. | |
| 4,904,260 A | 2/1990 | Ray et al. | |

(Continued)

FOREIGN PATENT DOCUMENTS

AU       25222/92 A1       9/1992

(Continued)

OTHER PUBLICATIONS

Alvin H. McKenzie, MD, "Fernstrom Intervertebral Disc Arthroplasty: A Long-Term Evaluation", Orthopaedics International Edition, vol. 2, No. 4, pp. 313-324, Jul./Aug. 1995.

(Continued)

*Primary Examiner*—Todd E. Manahan

(57) ABSTRACT

An intervertebral connection system having a fabric-based conformable ligament is disclosed herein.

57 Claims, 13 Drawing Sheets

U.S. PATENT DOCUMENTS

| | | | |
|---|---|---|---|
| 4,917,700 A | 4/1990 | Aikins | |
| 4,955,911 A | 9/1990 | Frey et al. | |
| 4,987,892 A | 1/1991 | Krag et al. | |
| 5,002,576 A | 3/1991 | Fuhrmann et al. | |
| 5,011,484 A | 4/1991 | Breard | |
| 5,022,855 A | 6/1991 | Jeckel | |
| 5,024,669 A * | 6/1991 | Peterson et al. | 623/13 |
| 5,049,155 A | 9/1991 | Bruchman et al. | |
| 5,074,864 A | 12/1991 | Cozad et al. | |
| 5,084,051 A | 1/1992 | Tormala et al. | |
| 5,102,421 A | 4/1992 | Anspach, Jr. | |
| 5,108,395 A | 4/1992 | Laurain | |
| 5,108,397 A | 4/1992 | White | |
| 5,112,332 A | 5/1992 | Cozad et al. | |
| 5,116,334 A | 5/1992 | Cozad et al. | |
| 5,147,359 A | 9/1992 | Cozad et al. | |
| 5,152,303 A | 10/1992 | Allen | |
| 5,154,718 A | 10/1992 | Cozad et al. | |
| 5,156,616 A | 10/1992 | Meadows et al. | |
| 5,157,111 A | 10/1992 | Pachence | |
| 5,171,273 A | 12/1992 | Silver et al. | |
| 5,180,393 A | 1/1993 | Commarmond | |
| 5,197,983 A | 3/1993 | Berman et al. | |
| 5,201,734 A | 4/1993 | Cozad et al. | |
| 5,222,987 A | 6/1993 | Jones | |
| 5,261,913 A | 11/1993 | Marnay | |
| 5,269,783 A * | 12/1993 | Sander | 606/72 |
| 5,306,308 A | 4/1994 | Gross et al. | |
| 5,330,473 A | 7/1994 | Howland | |
| 5,344,421 A | 9/1994 | Crook | |
| 5,346,492 A | 9/1994 | Morgan | |
| 5,376,118 A | 12/1994 | Kaplan et al. | |
| 5,380,324 A | 1/1995 | Muller et al. | |
| 5,380,328 A | 1/1995 | Morgan | |
| 5,384,149 A | 1/1995 | Lin | |
| 5,395,372 A | 3/1995 | Holt et al. | |
| 5,397,359 A | 3/1995 | Mittelmeier | |
| 5,405,391 A | 4/1995 | Henderson et al. | |
| 5,415,661 A | 5/1995 | Holmes | |
| 5,443,483 A | 8/1995 | Kirsch | |
| 5,453,227 A | 9/1995 | Rieger | |
| 5,456,722 A | 10/1995 | McLeod et al. | |
| 5,462,478 A | 10/1995 | Fredsby et al. | |
| 5,496,372 A | 3/1996 | Hamamoto | |
| 5,527,311 A | 6/1996 | Procter et al. | |
| 5,531,745 A | 7/1996 | Ray | |
| 5,531,747 A | 7/1996 | Ray | |
| 5,531,751 A | 7/1996 | Schultheiss et al. | |
| 5,536,274 A | 7/1996 | Neuss | |
| 5,540,703 A | 7/1996 | Barker, Jr. et al. | |
| 5,540,964 A | 7/1996 | Mallen | |
| 5,549,679 A | 8/1996 | Kuslich | |
| 5,562,671 A | 10/1996 | Goble et al. | |
| 5,562,736 A | 10/1996 | Ray et al. | |
| 5,571,109 A | 11/1996 | Bertagnoli | |
| 5,591,235 A | 1/1997 | Kuslich | |
| 5,601,554 A | 2/1997 | Howland et al. | |
| 5,609,634 A | 3/1997 | Voydeville | |
| 5,611,801 A | 3/1997 | Songer | |
| 5,628,756 A | 5/1997 | Barker, Jr. et al. | |
| 5,634,944 A | 6/1997 | Magram | |
| 5,645,596 A | 7/1997 | Kim et al. | |
| 5,674,295 A | 10/1997 | Ray et al. | |
| 5,674,296 A | 10/1997 | Bryan et al. | |
| 5,676,703 A | 10/1997 | Gelbard | |
| 5,681,310 A | 10/1997 | Yuan et al. | |
| 5,681,311 A | 10/1997 | Foley et al. | |
| 5,683,391 A | 11/1997 | Boyd | |
| 5,693,099 A | 12/1997 | Harle | |
| 5,709,683 A | 1/1998 | Bagby | |
| 5,711,960 A | 1/1998 | Shikinami | |
| 5,721,049 A | 2/1998 | Marcolongo et al. | |
| 5,735,899 A | 4/1998 | Schwartz et al. | |
| 5,741,253 A | 4/1998 | Michelson | |
| 5,766,176 A | 6/1998 | Duncan | |
| 5,766,254 A | 6/1998 | Gelbard | |
| 5,769,894 A | 6/1998 | Ferragamo | |
| 5,797,917 A | 8/1998 | Boyd et al. | |
| 5,800,543 A | 9/1998 | McLeod et al. | |
| 5,824,093 A | 10/1998 | Ray et al. | |
| 5,857,995 A | 1/1999 | Thomas et al. | |
| 5,865,846 A | 2/1999 | Bryan et al. | |
| 5,885,287 A | 3/1999 | Bagby | |
| 5,888,221 A | 3/1999 | Gelbard | |
| 5,888,223 A | 3/1999 | Bray, Jr. | |
| 5,899,902 A | 5/1999 | Brown et al. | |
| 5,906,828 A | 5/1999 | Cima et al. | |
| 5,925,056 A | 7/1999 | Thomas et al. | |
| 5,972,368 A | 10/1999 | McKay | |
| 5,989,256 A | 11/1999 | Kuslich et al. | |
| 6,010,502 A | 1/2000 | Bagby | |
| 6,022,376 A | 2/2000 | Assell et al. | |
| 6,031,148 A | 2/2000 | Hayes et al. | |
| 6,045,552 A | 4/2000 | Zucherman et al. | |
| 6,045,554 A | 4/2000 | Grooms et al. | |
| 6,077,076 A | 6/2000 | Comfort | |
| 6,086,589 A | 7/2000 | Kuslich et al. | |
| 6,090,998 A | 7/2000 | Grooms et al. | |
| 6,093,205 A | 7/2000 | McLeod et al. | |
| 6,099,568 A * | 8/2000 | Simonian et al. | 623/13.11 |
| 6,113,640 A | 9/2000 | Tormala et al. | |
| 6,120,503 A | 9/2000 | Michelson | |
| 6,121,172 A | 9/2000 | Marcolongo et al. | |
| 6,136,001 A | 10/2000 | Michelson | |
| 6,136,002 A | 10/2000 | Shih et al. | |
| 6,139,551 A | 10/2000 | Michelson et al. | |
| 6,143,036 A | 11/2000 | Comfort | |
| RE37,005 E | 12/2000 | Michelson et al. | |
| 6,156,037 A | 12/2000 | LeHuec et al. | |
| 6,156,067 A | 12/2000 | Bryan et al. | |
| 6,162,537 A | 12/2000 | Martin et al. | |
| 6,187,009 B1 | 2/2001 | Herzog et al. | |
| 6,293,949 B1 | 9/2001 | Justis et al. | |
| 6,296,643 B1 | 10/2001 | Hopf et al. | |
| 6,299,613 B1 | 10/2001 | Ogilvie et al. | |
| 6,312,431 B1 | 11/2001 | Asfora | |
| 6,332,894 B1 | 12/2001 | Stalcup et al. | |
| 6,336,940 B1 | 1/2002 | Graf et al. | |
| 6,361,538 B1 | 3/2002 | Fenaroli et al. | |
| 6,368,326 B1 | 4/2002 | Dakin et al. | |
| 6,554,852 B1 | 4/2003 | Oberlander | |
| 6,562,073 B2 | 5/2003 | Foley | |
| 6,576,017 B2 | 6/2003 | Foley et al. | |
| 6,585,769 B1 * | 7/2003 | Muhanna et al. | 623/13.14 |
| 6,607,530 B1 | 8/2003 | Carl et al. | |
| 6,616,694 B1 | 9/2003 | Hart | |
| 6,652,585 B2 | 11/2003 | Lange | |
| 2002/0107570 A1 | 8/2002 | Sybert et al. | |
| 2002/0107572 A1 | 8/2002 | Foley | |
| 2002/0120270 A1 | 8/2002 | Trieu et al. | |
| 2002/0123750 A1 | 9/2002 | Eisermann et al. | |
| 2002/0143329 A1 | 10/2002 | Serhan et al. | |
| 2003/0195514 A1 | 10/2003 | Trieu et al. | |

FOREIGN PATENT DOCUMENTS

| | | |
|---|---|---|
| DE | 2914164 C1 | 1/1991 |
| EP | 0304305 | 3/1987 |
| EP | 0353936 | 2/1990 |
| EP | 0 507 162 A1 | 3/1992 |
| EP | 0507162 | 10/1992 |
| EP | 0 520 177 A1 | 12/1992 |
| FR | 2 612 392 A1 | 3/1987 |
| FR | 2612392 | 9/1988 |

| FR | 2709410 | 9/1993 |
| NL | 1009471 C2 | 6/1998 |
| WO | WO 90/07304 A1 | 7/1990 |
| WO | WO 91/06249 A1 | 5/1991 |
| WO | WO 93/22989 A1 | 11/1993 |
| WO | WO 94/21185 A1 | 9/1994 |
| WO | WO 98/51226 A3 | 11/1998 |
| WO | WO 98/55053 | 12/1998 |
| WO | WO 99/47082 | 9/1999 |
| WO | WO 99/62439 | 12/1999 |
| WO | WO 00/03653 A2 | 1/2000 |
| WO | WO 00/59388 A1 | 10/2000 |
| WO | WO 00/64365 | 11/2000 |
| WO | WO 00/67651 A1 | 11/2000 |
| WO | WO 00/643262 A2 | 11/2000 |
| WO | WO 00/72782 A1 | 12/2000 |
| WO | WO 02/067793 A2 | 9/2002 |
| WO | WO 02/078571 A1 | 10/2002 |

OTHER PUBLICATIONS

G. Cremascoli, "Ligament de Verrouillage-suspension Orthese inter-eplno-lamaire de verrouillage Intervertebral a effet de suspension-delordose".

MP Grevitt, "The Graf Stabilsation system: Early Results in 50 Patients", European Spine Journal, 1995; 4(3): pp. 169-175.

Anterior Cruciate Ligament (ACL) Reconstruction Technique, Patellar Tendon Graft, Orthopaeic Associates of Portland, Sports Medicine Center, www. orthoassociates.com/acltech.htm, Douglas W. Brown, M.D., pp. 1-9, Sep. 27, 2000.

Anterior Cruciate Ligament (ACL) Graft Options, Orthopaedoc Associates of Portland, Sports MEdicine Center, www. orthoassociates.com/ACL grafts.htm, F. Lincoln Avery, M.D., pp. 1-10, Sep. 27, 2000.

PCL Reconstruction: Fixation Techniques; Wheeles' Textbook of Orthopaedics; www.medmedia.com/012/5000.htm, Sep. 27, 2000, p. 1 or 1.

Arthrotek Product Information, www.arthrotek.com and product literature; Sep. 27, 2000.

Graft Choices in ACL Reconstruction, Carleton Sports Medicine Clinic, www.carletonsportsmed.com/graftacl.htm, pp. 1-6, Sep. 27, 2000.

International Search Report PCT/US02/06138.

* cited by examiner

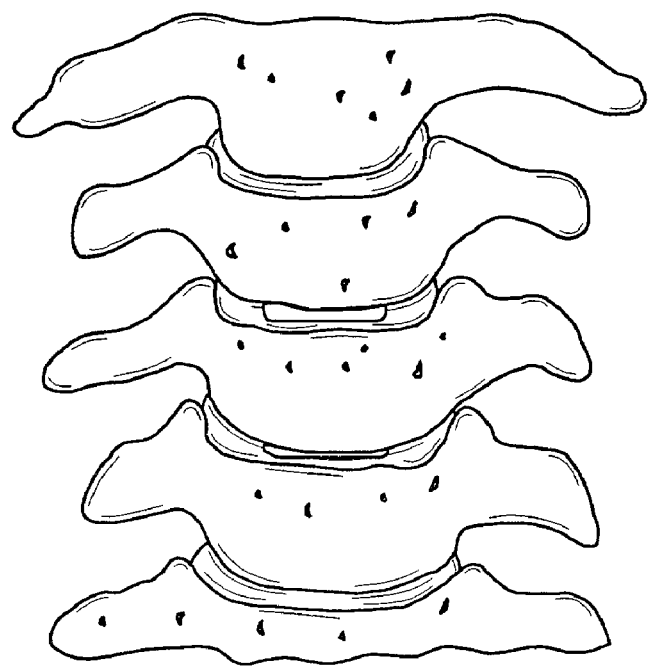
FIG. 9
PRIOR ART
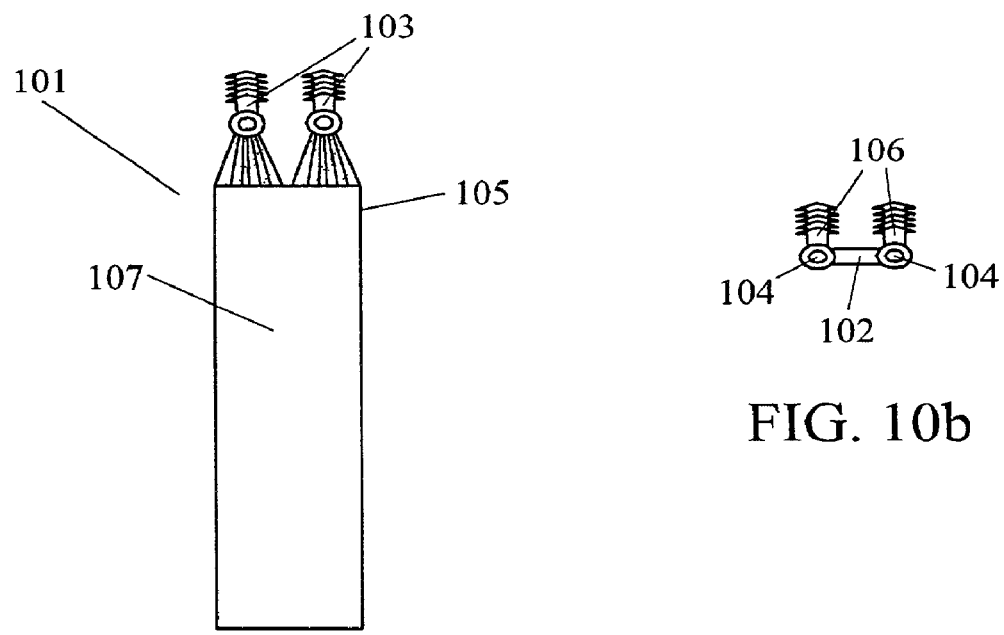
FIG. 10a
FIG. 10b

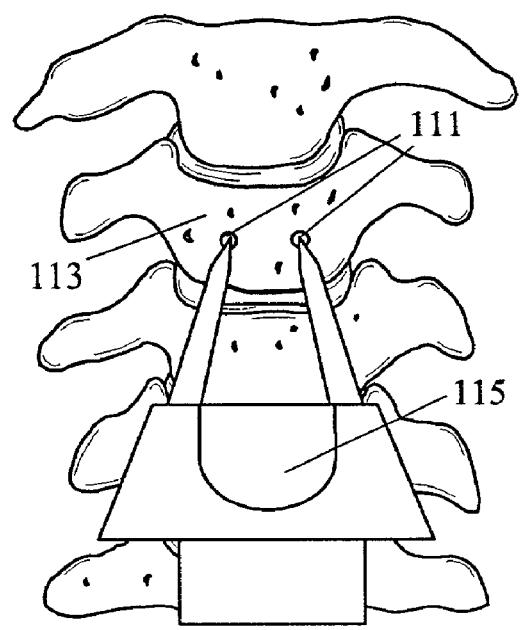
FIG. 11
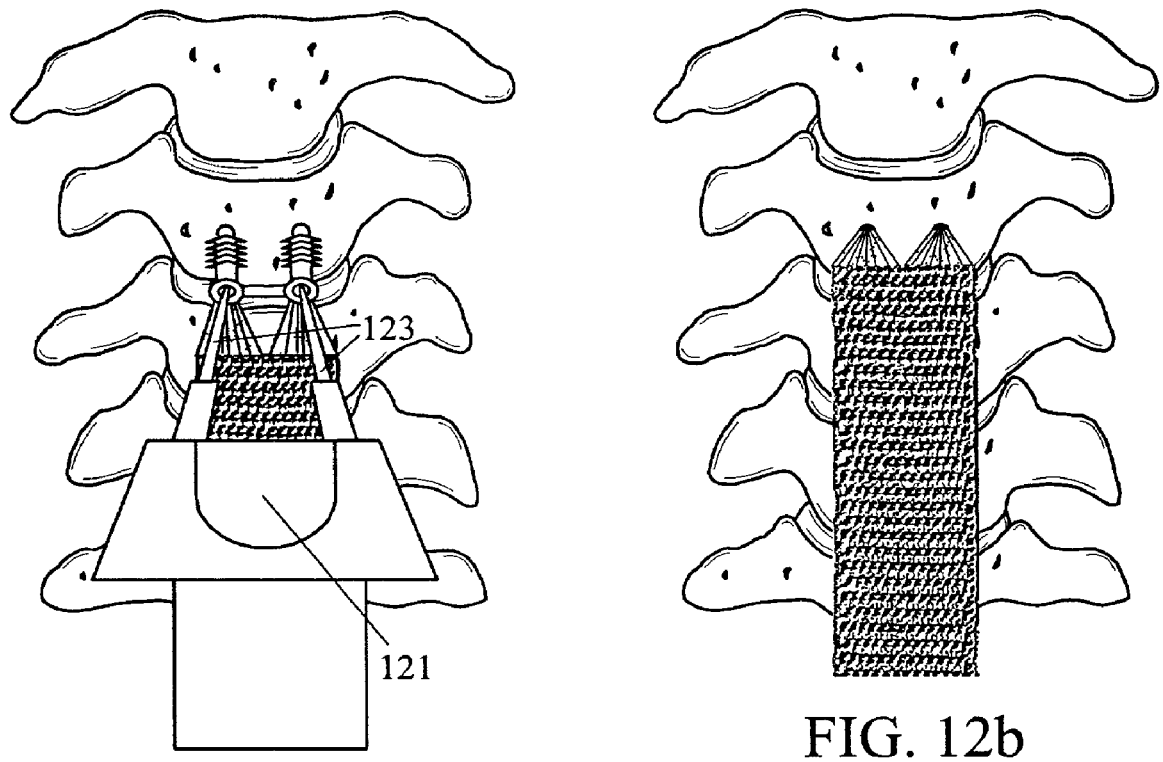
FIG. 12a
FIG. 12b

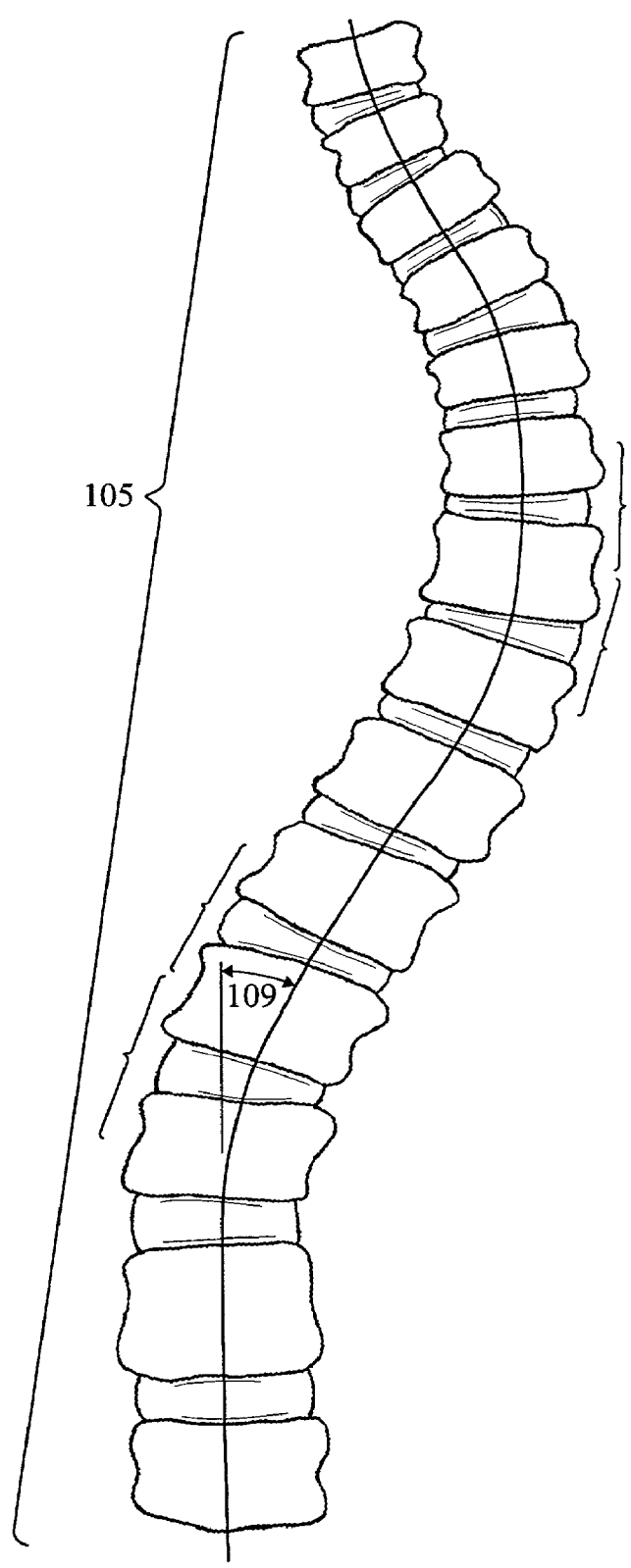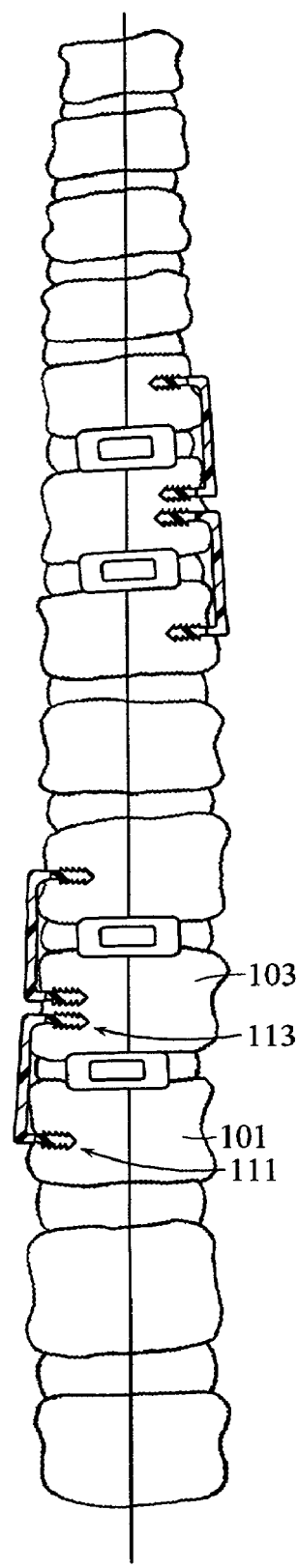
FIG. 16a
PRIOR ART
FIG. 16b

INTERVERTEBRAL CONNECTION SYSTEM

BACKGROUND OF THE INVENTION

Single level spine fusion procedure typically entails removing the intervertebral disk (not shown) and inserting an interbody device 2 into the disk space 4, as shown in FIG. 1.

Current spine fusion procedures rely heavily on the use of posterior fixation to achieve the stability and rigidity necessary to obtain successful clinical results. However, implantation of posterior instrumentation necessarily involves removing important musculoskeletal elements.

Because of these concerns, anterior fixation systems have also been developed which require removal of much less musculoskeletal mass. However, because anterior fixation, especially in the abdominal or thoracic area, lies in close proximity to vital internal organs such as the aorta, these fixation systems must also possess a low profile.

In general, conventional intervertebral connection systems can be characterized by ligament components which are either a) relatively rigid, or b) not shaped for cooperative connection to bone fasteners, or by bone fasteners which are shouldered to seat upon the vertebral surface. When the ligament is relatively rigid, it must essentially fully lie upon the anterior surfaces of the adjacent vertebrae, thereby limiting design options. Systems having relatively rigid ligaments typically have transverse holes near their end portions for accepting bone fasteners. In systems in which the ligament is not shaped for cooperative attachment to the bone fastener, attachment is typically made by either suturing or by passing a screw through the ligament. When the bone fastener is seated upon the vertebral surface, a portion of the bone fastener protrudes from the surface and the tension of the ligament can not be further adjusted.

U.S. Pat. No. 5,415,661 ("Holmes") discloses an implantable spinal assist device apparently intended for posterior use comprising a ligament 4 having opposed terminal ends 6. The opposed terminal ends have transverse openings for accepting a pair of undescribed conventional bone screws. Although the ligament can be "fully compliant", it receives its flexibility by designing a curve into central portion 10 and intermediate portions 12. Accordingly, the terminal portions 8a, 8b of the ligament are relatively straight and stiff and are preferably made of fiber/polymer composites. Since these terminal portions 8a, 8b are relatively rigid, the ligament must essentially fully lie upon the anterior surfaces of the adjacent vertebrae, thereby limiting design options.

In addition, if the Holmes device were used for anterior fixation, its lack of control of the bone screw profile could cause the screw head to protrude towards the aorta. Further, there is no teaching in Holmes that the ligament or screws could be bioresorbable.

U.S. Pat. No. 6,136,001 ("Michelson") discloses a spinal implant having an integral staple member 12 comprising top member 14 having projections 16, 17 at either end thereof for insertion into the adjacent vertebrae. There is no disclosure in Michelson that the any part of this staple member should be flexible. Accordingly, this staple does not provide the degree of flexibility provided by a natural ligament, and so is prone to failure during compression of the spine. Such a failure could spread device fragments about the area of the aorta and lungs. The rigidity of the staple also hinders the loading of the interbody fusion cage, thereby producing undesirable stress shielding. The rigidity of this staple also makes it unsuitable for use with intradiscal devices designed to provide a measure of motion (e.g., motion discs).

In addition, the Michelson staple has a thickness in the range of 2.0 mm to 4.0 mm and can be bioresorbable.

PCT Patent Publication No. WO 00/59388 ("Middleton") discloses an artificial spine ligament 100 comprising a conformable plate 102 having transverse longitudinal holes for accepting bone screws 114. Although Middleton teaches that the ligament should be conformable, the conformability feature appears to relate to the plate's ability to conform to the surface of the vertebral bodies, not to bend around corners. Accordingly, the preferred embodiment discloses an apparently monolithic polyethylene uniplanar-plate having transverse holes for accepting screws. These screws have shoulders which seat upon a countersunk portion of the transverse holes. In addition, since the five-piece assembly of Middleton is not integral, it allows for micromotion between the various components. Middleton discloses that the heads of the screws should be flush with the top surface of the plate. Middleton further discloses that the ability of the plate to accept tensile or compressive loads can be adjusted by changing the location of the screw in the transverse longitudinal holes. Lastly, there is no disclosure in Middleton of a bioresorbable component.

U.S. Pat. No. 5,180,393 ("Commarmond") discloses an artificial spinal ligament made of a flexible textile material having hollow eyelets at each end. Each eyelet is shaped to receive the head of a fixation screw. The ligament comprises a secondary winding which gives the ligament stiffness during compression, thereby providing stability to the system. The stiffness of this ligament would likely cause it stress if it were to be bent around a corner. Accordingly, the preferred embodiment discloses uniplanar ligaments. The eyelets of the Commarmond device include concave seats for seating screws. Once these screws are seated, the tension on the ligament can not be adjusted.

Respecting profile, Commarmond discloses dimensions of the ligament in the 5-10 mm range. In addition, the use of a conventional screw causes the device to protrude somewhat from the vertebral surfaces, and so it would be unsuitable for use in anterior applications. Respecting resorbability, Commarmond discloses a non-resorbable polyester ligament, and metal eyelets and screws.

U.S. Pat. No. 5,865,846 ("Bryan") discloses a motion disc-type of spinal prosthesis having a strap-like ligament 250 made of Kevlar-like and/or Goretex-like materials, which is attached to the vertebral bodies by screws 94. The preferred embodiment discloses a uniplanar strap attached to the vertebral bodies by transverse screws having shoulders which seat upon the strap.

Although Bryan discloses bioresorbable screws, since the ligament is made of Kevlar-like and/or Goretex-like materials, it is non-resorbing and so will permanently remain in the body.

A few references disclose flexible ligaments whose ends are not shaped for cooperative connection to bone fasteners. For example, U.S. Pat. No. 6,093,205 ("McLeod") discloses a spinal implant having a fabric element 40 which is secured across adjacent vertebrae by passing sutures therethrough to undescribed bone fasteners implanted into the adjacent vertebrae. The use of sutures as a ligament-bone fastener connection means is disadvantageous for many reasons. For example, because sutures are typically weak, they are prone to failure, thereby risking detachment of one end of the ligament in the vicinity of the aorta. They produce localized stresses in the portions of the ligament and bone fastener to which they attach. Their resorption time is often far too quick to be suitable for use as part of a vertebral connection system in spinal fusion. Lastly, their fixation must occur intraoperatively, thereby increasing the duration and difficulty of the operation. Although fabric element 40 may be made of bioresorbable materials, there is no disclosure in McLeod that the bone fastener should be bioresorbable.

U.S. Pat. No. 5,681,310 ("Yuan") discloses a spinal fixation device comprising a flexible mat 10 fastened across the invertebral space by fastening elements 20. Although Yuan discusses bioabsorption of the device components, the materials disclosed therein as those suitable for use as components, such as DACRON and metals, do not bioabsorb within about 24 months and so do not accommodate growth of the patient. Thus, this system may not be desirable for applications in which the patient may not yet be fully-grown. Further, FIG. 5 of Yuan discloses a fastening screw 20" having a fastening cord 25 attached thereto, wherein the screw 20" is inserted through the mat 10 and into the vertebra, and then is secured by the fastening cord. A portion of the mat 10 is thus destroyed during the attachment process. Further, Yuan does not disclose any means for increasing tension upon the fastened ligament. Lastly, the intraoperative attachment of the mat to the screw increases both the duration and difficulty of the operation.

Many generic ligament repair devices have been described. For example, PCT Patent Publication No. WO 91/06249 ("Collins") discloses a prosthetic ligament attached to the bone via staples. PCT Patent Publication No. WO 00/72782 ("Wolowacz") discloses a flexible elongate tape fixed to the bone by either staples, bone fasteners, or screw-washer combinations, optionally in combination with a "figure of eight" eyelet loop at the end of the device.

Thus there is a need for an intervertebral connection system which can easily connect a compliant ligament to a bone fastener without significantly straining the ligament, without suturing, and without destroying a portion of the ligament.

SUMMARY OF THE INVENTION

In accordance with the present invention, the present inventors have developed an intervertebral connection system which overcomes many of the deficiencies in the prior art.

In one aspect of the present invention, the present inventors have developed a system in which a ligament has conformable portions and end portions shaped to cooperatively connect to shoulderless bone fasteners. The shoulderless feature of the bone fastener allows the bone fastener to be fully driven into the vertebral surface, thereby eliminating any problematic protrusion while also providing a means to adjust the tension of the ligament after the bone fasteners have been located. The conformable portions of the ligament allow the ligament to conform to the recess produced by a fully driven bone fastener without generating undue stress, thereby accommodating the surgeon's desire to fully drive the bone fastener within the recess. The cooperative shape of the ligament end portions allows for non-destructive attachment of the ligament to the bone fasteners without the use of sutures, thereby minimizing unwanted connection-related stresses and undesirable generation of foreign particles within the patient.

Accordingly, this invention allows the ligament to provide the secure, very low profile attachment required for spine stabilization without the disadvantages of either suturing or destructive attachment common to conventional systems.

In one embodiment, cooperative connection is accomplished by integrally bonding each end portion of the ligament to its corresponding bone fastener prior to placement of the ligament upon the anterior surfaces of the vertebrae, preferably during an injection molding process.

Therefore, in accordance with the present invention, there is provided an intervertebral connection system comprising:
a) a ligament having:
    i) a central portion,
    ii) first and second end portions, and
    iii) first and second conformable portions, wherein the first conformable portion is disposed between the central portion and the first end portion, and the second conformable portion is disposed between the central portion and the second end portion, and b) first and second shoulderless bone fasteners, wherein the first and end portion is shaped to cooperatively connect to the first bone fastener, and the second end portion is shaped to cooperatively connect to the second bone fastener.

SUMMARY OF THE FIGURES

FIG. 3c is a cross-section of the pivot of FIG. 3a.

FIG. 9 presents an aerial view of a conventional two-level discectomy, wherein each intervertebral disc has been replaced with a fusion cage.

FIG. 10a is an aerial view of a two-level embodiment of the present invention.

FIG. 10b presents a secondary bone fastener for use with the two-level embodiment of the present invention.

FIG. 11 presents an aerial view of the step of providing two recesses upon the anterior surface of each vertebrae.

FIG. 12a a presents an aerial view of the step of inserting each bone fastener of FIG. 10a into the recess in the anterior surfaces using a preferred insertion tool.

FIG. 12b presents an aerial view of the fixation of adjacent vertebrae by the system of the present invention, wherein the bone fasteners are fully inserted into the recesses.

FIG. 16a presents a conventional thoracolumbar scoliotic spine.

FIG. 16b presents the use of the system of the present invention resulting in a straighteneing of the scioliotic spine.

DETAILED DESCRIPTION OF THE INVENTION

For the purposes of the present invention, a "conformable" portion of the ligament can be bent approximately 90°, more preferably approximately 120°, around a corner with a radius of approximately 1 mm without causing a strain in the portion that is at least 75% of the failure strain. Such a feature will allow the device to be easily inserted into a hole in the vertebral body and conform to the anterior surface without causing damage to the device. A "compressible" portion of the ligament can accommodate displacements generated by normal spinal compression by flexing, buckling and/or relieving pretension imposed on the ligament at the time of insertion. Some materials may be flexible but not compressible. An "extensible" portion of the ligament can accommodate displacements generated by normal spinal extension by increasing in length at least 20% without exceeding its yield point. Some materials can be "compressible" and/or "extensible" without being "conformable". A "tensionable" portion of the ligament can accommodate a pretension imposed on the ligament at the time of insertion. "Bioresorbable" means that the material loses at least 50% of its tensile strength within 24 months of implantation. "Pre-connected" means two components are attached prior to their placement upon the spine. A "shoulderless" bone fastener has no shoulder capable of seating upon the vertebral surface in a degree sufficient to prevent further driving of the bone fastener into the vertebral body. "Cooperative connection" means the components connect in a non-destructive way without the uses of sutures.

Figure 1:
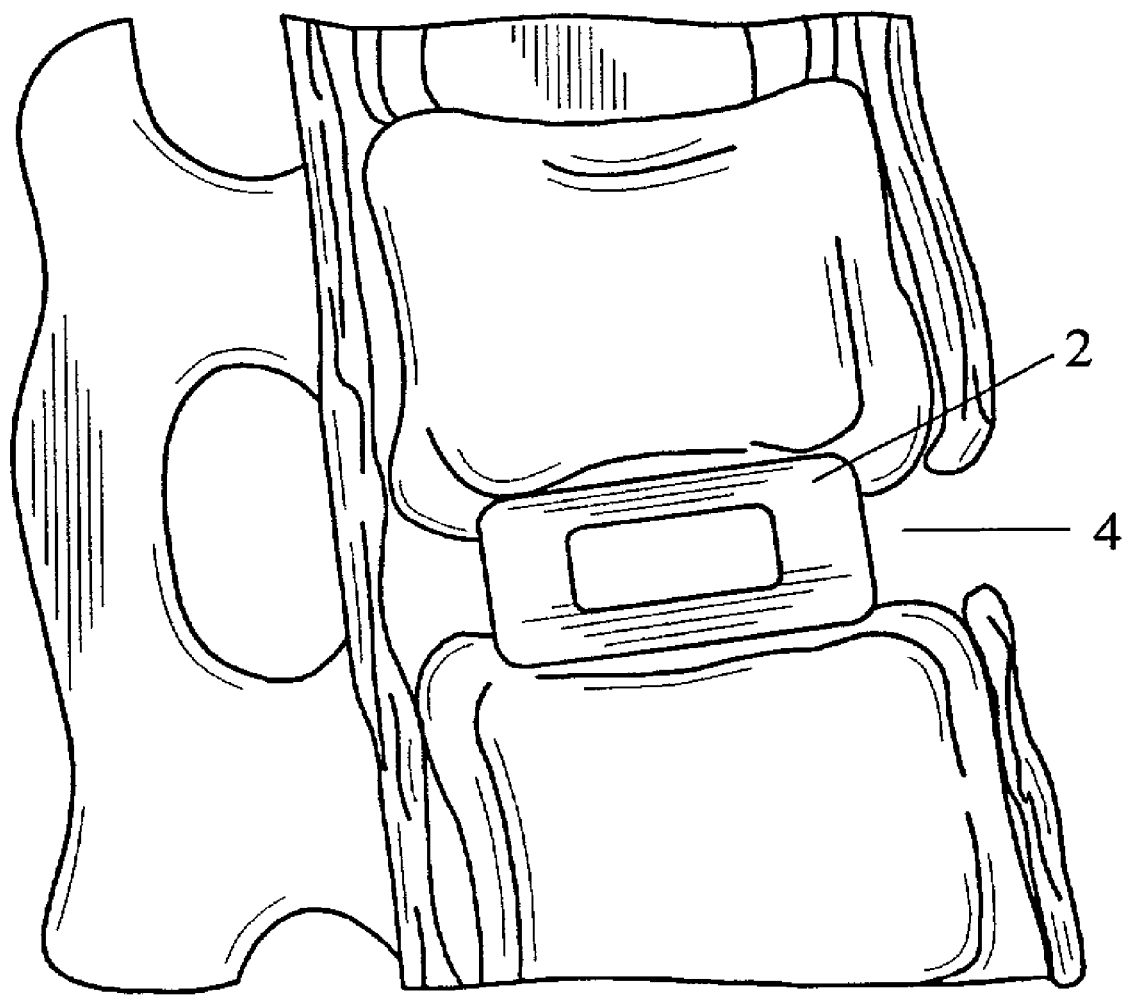
FIG. 1 is a cross-sectional view of a conventional fusion of adjacent vertebral segments, wherein the intervertebral disc has been replaced with a fusion cage.
Figure 2A:
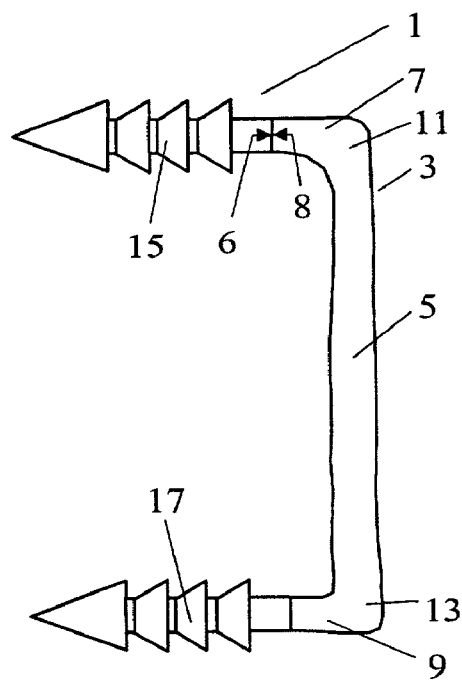
FIGS. 2a and 2b are side and aerial views of the system of the present invention.
Figure 2B:
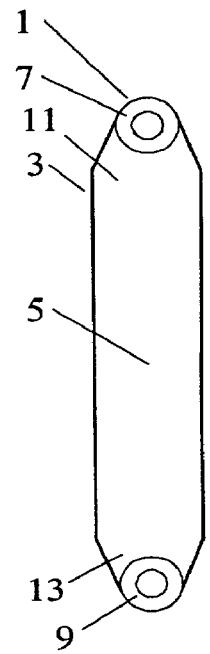

Now referring to FIGS. 2a and 2b, there is provided an intervertebral connection system 1 comprising:

a) a ligament 3 having:
  i) a central portion 5,
  ii) first and second end portions 7, 9, and
  iii) first and second conformable portions 11, 13, wherein the first conformable portion is disposed between the central portion and the first end portion, and the second conformable portion is disposed between the central portion and the second end portion, first and second shoulderless bone fasteners 15, 17, wherein the first end portion 7 is shaped to cooperatively connect to the first bone fastener 15, and the second end portion 9 is shaped to cooperatively connect to the second bone fastener 17.

In one especially preferred embodiment of the present invention, the system is intended to act as a temporary stabilization system for spine fusion procedures. That is, the system provides only temporary stabilization of the spine until the desired fusion can be achieved. Once fusion has been achieved, the system of this embodiment serves no further purpose. Therefore, in some embodiments, at least the central portion is made of a bioresorbable material. Preferably, the conformable portions are also made of a bioresorbable material. Preferably, the end portions of the ligament are also made of a bioresorbable material. Also preferably, the bone fasteners are also made of a bioresorbable material.

Preferred bioresorbable materials which can be used to make components of the present invention include bioresorbable polymers or copolymers, preferably selected from the group consisting of hydroxy acids, (particularly lactic acids and glycolic acids; caprolactone; hydroxybutyrate; dioxanone; orthoesters; orthocarbonates; and aminocarbonates. Preferred bioresorbable materials also include natural materials such as chitosan, collagen, cellulose, fibrin, hyaluronic acid; fibronectin, and mixtures thereof. However, synthetic bioresorbable materials are preferred because they can be manufactured under process specifications which insure repeatable properties.

A variety of bioabsorbable polymers can be used to make the device of the present invention. Examples of suitable biocompatible, bioabsorbable polymers include but are not limited to polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, χ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, χ,χ-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide, D,L-lactide, lactic acid, glycolide, glycolic acid, para-dioxanone, trimethylene carbonate and ε-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

Preferably, the bioresorbable material is selected from the group consisting of poly(lactic acid) ("PLA") and poly(glycolic acid)("PGA"), and copolymers thereof. These materials are preferred because they possess suitable strength and biocompatibility, display desirable resorption profiles, and have a long history of safe in vivo use. In general, PLA is a desirable because it typically has a resorption time exceeding 12 months, whereas PGA resorbs fairly quickly (having a resorption time of less than 12 months). However, PLA can require many years to completely resorb, and so is more likely to produce foreign-body reactions. Therefore, more preferably, the material is a PLA/PGA copolymer, more preferably the copolymer comprises between 80 wt % and 99 wt % lactic acid (as PLA), and between 1 wt % and 20 wt % glycolic acid (as PGA). Copolymers within these ranges provide the proper balance between the strength and the resorption time of the ligament.

Preferably, the bioresorbable component retains at least 50% of its tensile strength 6 months after implantation, but loses at least 50% of its tensile strength within 12 months of implantation. When this window of bioresorption is achieved, the component has the strength necessary to carry out its intended purpose during the time when bony fusion is occurring, but also bioresorbs after such fusion normally takes place. Also preferably, the bioresorbable polymer retains at least 50% of its mass 6 months after implantation, but loses at least 90% of its mass within 2 years of implantation. This may be accomplished by use of an 95/5 PLA/PGA copolymer.

In one preferred embodiment, both the compressible ligament and the bone fastener are each bioresorbable. The bioresorbable aspect of this device minimizes long term foreign body effects, while the compressible aspect minimizes the chances of short term failure by compressive loading. Therefore, in accordance with the present invention, there is provided an intervertebral connection system comprising:
a) a compressible ligament comprising first and second end portions, and
b) first and second bone fasteners, wherein each bone fastener and the ligament are bioresorbable.

In some embodiments, the materials and geometries are chosen so that the ligament resorbs before the bone fasteners. Such an embodiment minimizes the chances that foreign bodies (i.e., ligament portions) will become loose within the body after resorption of the bone fasteners. More preferably, the ligament is also tensionable, thereby minimizing the chances of short term failure by excessive extension.

In another preferred embodiment, the device has a compressible bioresorbable ligament whose end portions are shaped for cooperative attachment to the bone fasteners. The combination of bioresorbability, flexibility and cooperative attachment provides greater long term safety of the device. Therefore, in accordance with the present invention, there is provided an intervertebral connection system comprising:
a) a compressible ligament comprising first and second end portions and having at least one bioresorbable portion, and
b) first and second bone fasteners, wherein the first end portion is shaped to cooperatively connect to the first bone fastener, and the second end portion is shaped to cooperatively connect to the second bone fastener.

In some embodiments having bioresorbable materials, the system has advantageous use in conjunction with a motion disc. A motion disc typically comprises a flexible member sandwiched between a pair of rigid endplates. Accordingly, a motion disc differs from a conventional fusion device in that the motion disc has a flexibility which allows the adjacent vertebrae to move relative to each other after osteointegration of their endplates to the disc prosthesis has taken place. When a bioresorbable ligament is selected, the resorption time of the ligament can be tailored such that the ligament resorbs slightly after the osteointegration of the motion disc endplates occurs. When the ligament portion bioabsorbs, the motion disc is free to flex. In this case, the resorption feature eliminates any concern that the ligament will restrain the motion afforded by the motion disc. Particularly preferred motion discs include those described in U.S. Pat. No. 5,824,094 ("Serhan et al.").

Therefore, in accordance with the present invention, there is provided a kit comprising:
a) an intervertebral connection system comprising:
   i) a ligament comprising first and second end portions, and a central portion disposed therebetween, and having at least one bioresorbable portion, and
   ii) first and second bone fasteners, wherein the first bone fastener is shaped to cooperatively connect to the first end portion of the ligament, and the second bone fastener is shaped to cooperatively connect to the second end portion of the ligament, and
b) a motion disc having a first height, wherein the central portion of the ligament is bioresorbable and has a length, and wherein the length of the central portion is no less than the height of the motion disc.

Although bioresorbable materials are the preferred materials of construction for the components of the present invention, these components may be made from any material appropriate for human surgical implantation, including but not limited to all surgically appropriate metals including titanium, titanium alloy, chrome alloys and stainless steel, and non-metallic materials such as permanent or bioresorbable materials such as carbon fiber materials, resins, plastics and ceramics. If a nonbioresorbable material is selected, then preferred materials include polyesters, (particularly aromatic esters such as polyalkylene terephthalates, polyamides; polyalkenes; poly(vinyl fluoride); polyurethanes; polytetrafluoroethylene PTFE; carbon fibres; silk; and glass, and mixtures thereof.

Preferably, the central portion of the ligament has a width sufficient to keep the interbody graft or device within the intervertebral disc space. It should also have a length which is at least as great as a typical disc space (i.e., at least 1.5 to 2 cm in length) so that the conformable portions reach the adjacent vertebral bodies. Accordingly, it should have a high failure load in longitudinal tension. Preferably, this failure load is at least 500 N. It should also accommodate compression of the spine, preferably by flexing.

The width of the central portion is preferably between about 3 mm and 30 mm, more preferably between about 10 mm and 15 mm. When the central portion is made of a material having a tensile strength of at least about 50 MPa, it is strong enough to be used in these relatively short widths (as compared, e.g., to the ligaments of Yuan and McLeod) without breaking. In comparison, the ligaments of both Yuan and McLeod are much wider, and so have a greater likelihood of adversely contacting sensitive soft tissue structures such as the aorta and the trachea. Preferably, the strong material is a braided yarn.

The thickness of the central portion is preferably between about 0.5 and 5 mm. When the thickness of the central portion is not more than 5 mm, the potential for the central portion to rub against sensitive soft tissue structures is markedly diminished. When the thickness of the central portion is at least 0.5 mm, the central portion has the strength suitable for use in an intervertebral body connection system. More preferably, the thickness is between 1 mm and less than 2 mm. In this range of 1 mm to less than 2 mm, the central portion has both good strength and low profile. Without wishing to be tied to a theory, it is believed that the rigid staple of Michelson requires a thickness of at least 2 mm because of the load-bearing requirements of the device (i.e., it is intended to resist physiologic compression of the spine). Therefore, in accordance with the present invention, there is provided an intervertebral connection system comprising a central portion having a thickness of between 0.5 mm and less than 2 mm, preferably between 0.5 mm and less than 1.5 mm, more preferably between 1.0 mm and 1.5 mm, still more preferably between 1.0 mm and 1.2 mm.

Preferably, at least the anterior face of the central portion of the invention is not sufficiently rough to cause irritation to the surrounding soft tissue structures, such as the esophagus and the aorta. For textile structures, preferably, the individual filaments that are used to form the device are smooth and round. Smooth and round fibers can be made, for example, using a melt spinning process with a circular die to form the fibers. Furthermore, the textile structure is preferably made with continuous fibers rather than short fibers. Examples are woven and braided structures as opposed to felt structures.

Preferably, the conformable portions of the ligament have sufficient flexibility to partially lie flat against the vertebral surface and bend about 90 degrees in order to enter a recess in the bone to connect the central portion (which lies flat against the bone) to the bone fastener (which is disposed orthogonal to the surface) without experiencing significant additional stress. If the conformable portions are also tensionable, they also offer a means of providing tension to the ligament.

Preferably, conformability in the conformable portions is provided by constructing them as fabrics. The fabric may be formed by a flat or circular weaving, knitting, braiding, crocheting or embroidery. Preferably, the fabric is braided in order to provide highest tensile strength. Preferred materials suitable for use as fabrics include polyester, polypropylene, polyethylene, carbon fiber, glass, glass fiber, polyurethane, polyaramide, metals, polymers, copolymers, polyactic acid (PLA), polyglycolic acid (PGA), silk, cellusoseic acid, and polycaprolactone fibers.

Preferably, the conformable portion can conform to a surface having a 90 degree bend and produce stress which is less than 60% of the material's yield or failure strain.

In another aspect of the present invention, the central and conforming portions have differing widths. In particular, when the central portion has a larger width than the conforming portion, a portion of each conforming portions can more easily enter the vertebral recess while the central portion provides sufficient areal coverage of the vertebrae. Therefore, in accordance with the present invention, there is provided an intervertebral connection system comprising:
a) a ligament having:
 i) a central portion,
 ii) first and second end portions, and
 ii) first and second conformable portions, wherein the first conformable portion is disposed between the central portion and the first end portion, and the second conformable portion is disposed between the central portion and the second end portion, wherein the width of the conforming portion is smaller than the width of the central portion.

Preferably, the central portion width is at least 1.5 times larger than the smallest width of the conforming portion, more preferably at least 3 times larger.

The combined length of the central portion and conforming portions is preferably between about 15-110 mm, more preferably between about 20-50 mm.

In some embodiments, it is desirable to tailor the ligament to fail in its central portion in order to minimize the length of foreign bodies which can float freely within the body. In general, controlled strength loss in the ligament may be accomplished by either selecting materials based upon their typical resorption times or by providing designs which selectively favor resorption of certain ligament portions. In one embodiment, the ligament has a relatively thin central portion. This thinner portion should fail sooner than the end portions. Another embodiment provides a first material in the central portion which has a relatively short resorption time and a second material in the conforming or end portions which have a relatively long resorption time. In this condition, the bioresorption of the first material will more quickly cause failure of the ligament in that central portion. By using different materials to engineer the differential resorption, the desired geometry of the ligament noted above need not be altered.

Therefore, in accordance with the present invention, there is provided an intervertebral connection system comprising:
a) a ligament having:
 i) a central portion,
 ii) first and second end portions, and
 iii) first and second conformable portions, wherein the first conformable portion is disposed between the central portion and the first end portion, and the second conformable portion is disposed between the central portion and the second end portion
b) first and second shoulderless bone fasteners, wherein the first end portion is connected to the first bone fastener, and the second end portion is connected to the second bone fastener, and wherein the central portion is made of a first material having a first resorption time, the end portion is made of a second material having a second resorption time, and the first material has a shorter resorption time than that of the second material.

Figure 2C:
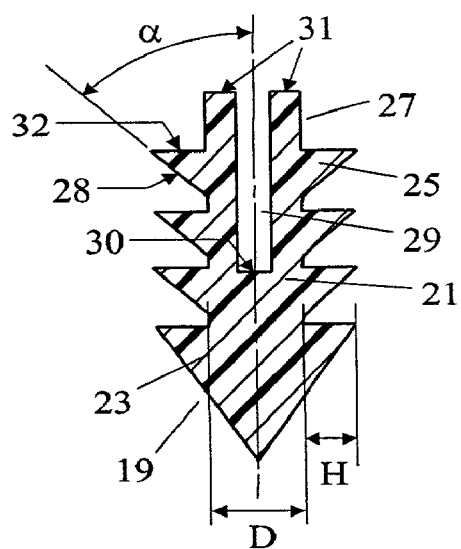
FIG. 2c is a cross-section of a bone fastener of the present invention.
Figure 2D:
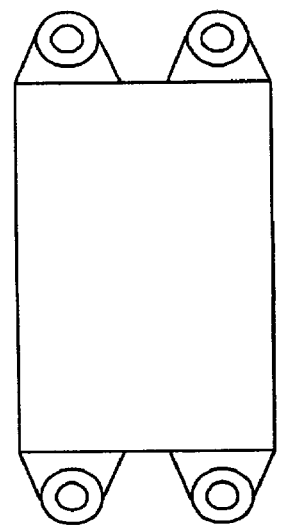
FIG. 2d is an aerial view of one embodiment of the present invention in which four end portions of the ligament share a common central portion.
Figure 3A:
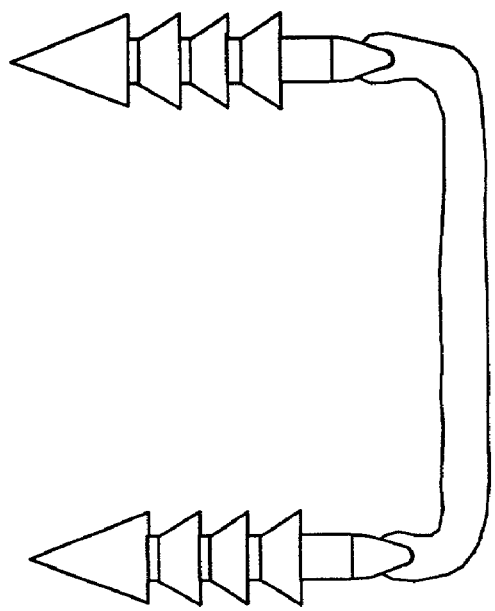
FIGS. 3a and 3b present embodiments of the present invention having a pivot connection.
Figure 3B:
Figure 3C:
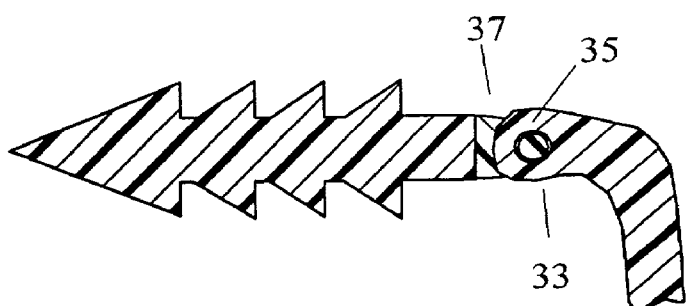
Figure 3D:
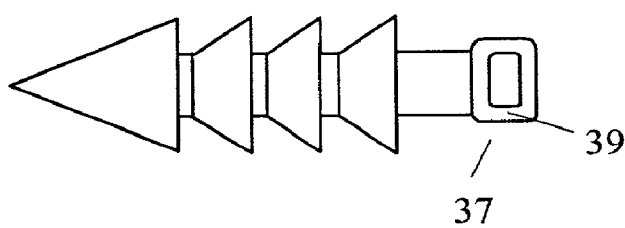
FIG. 3d presents a bone fastener having a closed hook suitable for use in a pivot connection.

In another embodiment of this invention, the ligament body is wider, preferably between 10–30 mm, more preferably between 15–20 mm and has two anchors at each end of the ligament, as shown in FIG. 2d. In this configuration, the ligament device is better able to resist physiological motions in lateral bending and axial rotation. Furthermore, with four anchors, there is less concern regarding anchor pullout.

In some embodiments, however, at least the central and end portions of the ligament are made of the same material. When the materials are so selected, these portions may be easily made and pre-connected in an integral fashion. Preferably, the material selected is bioresorbable. More preferably, it is a PLA/PGA copolymer, more preferably the material comprises between 80 wt % and 99 wt % lactic acid (as PLA) and between 1 wt % and 20 wt % glycolic acid (as PGA). Also preferably, the material has a textile form, such as a braided or woven yarn.

Preferably, at least one of the central portion and conforming portion is extensible. When one of these components is extensible, the ligament is able to elongate when the adjacent vertebral bodies are in extension, thereby reducing the likelihood of rupture. Preferably, the length of the extensible portion can be increased by 25% without exceeding its yield point. Preferably, this extensible material is made in a braided form. Because in some preferred embodiments, the central portion of the ligament is at least two times longer than either conforming portion, preferably the central portion is extensible.

Preferably, both the central portion and conforming portions are tensionable. When each portion is tensionable, the tension upon the ligament can be increased by simply further driving the bone fasteners into the vertebral bodies. The resulting tension produced in the tensionable body provides compressive load on the interbody device, thereby stabilizing the instrumented functional spinal unit (FSU). Preferably, this tensionable portion is made in a braided form.

Preferably, the end portion of the ligament is made of the same material of its adjacent conformable portion. Preferably, it is shaped to cooperatively connect to the attachment end of the bone fastener.

Now referring to FIG. 2c, preferably, the bone fastener 19 comprises a longitudinal shank 21, an insertion end 23 comprising protrusions 25 laterally extending from the shank, and an attachment end 27 having an upper surface 31 for connecting to the ligament. The function of the bone fastener is to securely fasten the central portion of the ligament across the disk space. The fastener may be any design known in the art, including winged, barbed or screw-in mechanisms. Preferably, the bone fastener is a barbed anchor, as it prevents pullout and is easily inserted.

In another aspect of the present invention, the attachment end 27 of the bone fastener is configured to accept a driver element. When this configuration is selected, the bone fastener may be driven into the bone by simply providing axial force to the upper surface 31 of the bone fastener through the driver. Therefore, in accordance with the present invention, there is provided an intervertebral connection system comprising:

a) a ligament comprising first and second end portions, and
b) first and second bone fasteners, wherein the first bone fastener is connected to the first end portion of the ligament, and the second bone fastener is connected to the second end portion of the ligament, and wherein the first bone fastener is configured to accept a driver.

Preferably, the configuration defines a recess 29 upon the upper surface 31 of the attachment end 27 of the bone fastener. This recess 29 is configured to accept the driver (not shown).

In some embodiments, the recess 29 of the bone fastener may be configured to allow insertion of a rescue screw, thereby allowing retrieval of the bone fastener.

Still referring to FIG. 2c, preferably, the lateral protrusions have leading edges 28 which define an angle a of no more than 45 degrees relative to the axis of the shank. In such embodiments, the bearing of the leading edge against the vertebral body surface will not substantially impede the progress of the bone fastener into the bone. Preferably, the leading edges define an angle of no more than 30 degrees, and more preferably between about 20 degrees and 30 degrees. When the angle $\alpha$ is between 20 and 30 degrees, the angle is sufficiently small to not impede the progress of the bone fastener, and yet sufficiently large to insure its secure fit.

In some embodiments, the height H of the protrusions on the bone fastener is no more than 70% of the diameter D of the longitudinal shank. When this condition is selected, the risk that any protrusion will act as a shoulder and stop further entry of the bone fastener into the vertebra is minimized. Preferably, the H/D ratio is no more than 40%, more preferably between about 20% and 40%. Within this more preferred window, the protrusion height is sufficiently small to not impede the progress of the bone fastener, and yet sufficiently large to insure its secure fit.

The outer diameter (2H+D) of the bone fastener is preferably between about 3–9 mm, more preferably about 4–6 mm. The length $L_{BF}$ of the bone fastener is preferably between about 3–45 mm, more preferably between about 15–25 mm.

Although the bone fasteners are selected to be bioresorbable in many embodiments of the present invention, in some embodiments, the attachment end of the bone fastener is made of a ceramic material. When the bone fastener is ceramic, it can withstand the high impact of the driver without failing. Therefore, in accordance with the present invention, there is provided an intervertebral connection system comprising:

a) a compressible ligament comprising first and second end portions, and
b) first and second bone fasteners, each bone fastener having an attachment end comprising a ceramic material and a shank comprising a polymer material.

In another aspect of the present invention, the bone fastener is bioresorbable and shoulderless. The shoulderless feature allows the bone fastener to be fully driven into the bone, thereby eliminating any protrusion and allows the surgeon to control the tension of the ligament by simply advancing the bone fastener, while the bioresorbable feature minimizes any long term effects the bone fastener may have on the patient. Therefore, in accordance with the present invention, there is provided an intervertebral connection system comprising:

a) a conformable ligament comprising first and second end portions, and
b) first and second bone fasteners, wherein the first bone fastener is connected to the first end portion of the ligament, and the second bone fastener is connected to the second end portion of the ligament.

wherein the bone fastener is bioresorbable and is shoulderless.

In another aspect of the present invention, the system has an integral design, whereby the compressible ligament and bone fasteners are integrally connected prior to insertion. The integral nature of this invention essentially eliminates any micromotion between the components. Therefore, in accordance with the present invention, there is provided an intervertebral connection system comprising:

a) a conformable ligament comprising first and second end portions, and
b) first and second bone fasteners, wherein the first bone fastener is integrally connected to the first end portion of the ligament, and the second bone fastener is integrally connected to the second end portion of the ligament.

In some embodiments, the width $W_L$ of the end portion of the ligament can be selected so as to be no more than (and preferably substantially the same dimension as) the width $W_{BF}$ of the attachment end of the bone fastener head. In this condition, the end portion can easily follow the bone fastener into the vertebral recess, thereby allowing the surgeon to control the tension of the ligament by simply advancing the bone fastener. When these widths are substantially the same, the strength of the system is optimized.

In another aspect of the present invention, the bone fastener is located within 5 mm of the end of the end portions of the ligaments. In this construction, the bone fastener may easily enter the recess without experiencing significant circumferential resistance from the conforming portion. Therefore, in accordance with the present invention, there is provided an intervertebral connection system comprising:

a) a conformable ligament comprising first and second end portions, and
b) first and second bone fasteners, wherein of the first bone fastener is located at the end of the first end portion.

Preferably, the bone fastener is located at the end of the end portion, as shown in FIG. 2a.

Now referring to FIG. 2a, in some embodiments, the attachment end of the bone fastener has an upper surface 6 and the terminus 8 of the end portion of the ligament body is attached to the upper surface of the bone fastener to provide an axial connection. When the bone fastener and the terminus are in axial alignment, as in FIG. 2a, very little strain is imparted to the connection during bone fastener insertion. These embodiments are desirable in cases in which the system can be put in tension by simply driving the bone fastener deeper into the vertebra, and in the case of the driver port through-hole discussed above.

Now referring to FIG. 3, in a third embodiment of this invention, end portions 33 of the ligament comprises first and second loops 35 while attachment end 37 of the bone fastener comprises a closed hook 39. Each loop can be securely and pivotally attached to its respective hook, thereby allowing the connection to pivot freely while the device is inserted and the anchor can be buried into the vertebral body. This pivoting feature provides high strength connection with free rotational movement to assist with ease of implementation. Therefore, in accordance with the present invention, there is provided an intervertebral connection system comprising:

a) a ligament comprising first and second end portions, and
b) first and second bone fasteners, wherein the first end portion is pivotally connected to the first bone fastener, and the second end portion is pivotally connected to the second bone fastener.

Figure 4A:
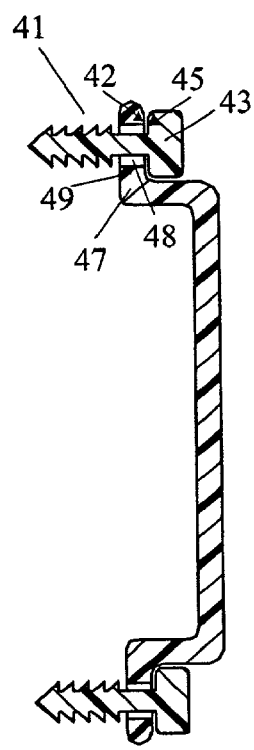
FIGS. 4a and 4b present side and aerial views of a system of the present invention having a washer.
Figure 4B:
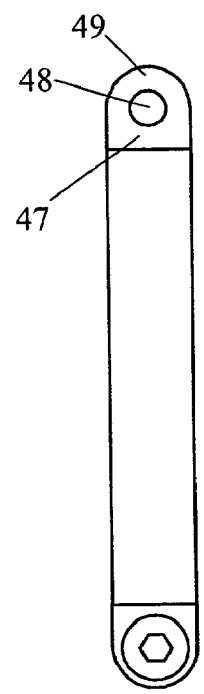

Now referring to FIGS. 4a and 4b, in other embodiments, the bone fastener 41 has an attachment end 43 having a lower surface 45 and the end portion 47 of the ligament comprises a washer 49 having an upper surface 42. Preferably, the bone fastener is a screw. Preferably, the washer is comprised of a solid, uniform material that is integrally connected to the ligament body, which is preferably comprised of braided yarns. In this case, the lower surface 45 of the attachment end bears against upper surface 42 of the washer. When the screw is used to secure the attachment end of the ligament, the solid, smooth mating surfaces minimize rotation of the washer and thus prevent twisting, elastic/plastic deformation, and/or damage to the ligament. These embodiments are desirable in cases in which the surgeon desires to fasten the ligament by a screw mechanism.

Therefore, in accordance with the present invention, there is provided an intervertebral connection system comprising:

a) a ligament having:
  i) a central portion,
  ii) first and second end portions, and
  iii) first and second intermediate portions, wherein the first intermediate portion is disposed between the central portion and the first end portion, and the second intermediate portion is disposed between the central portion and the second end portion, and b) first and second bone fasteners, wherein the first end portion has an upper surface, a lower surface and a first transverse hole therethrough, the hole having a shape for receiving the first bone fastener, and the second end portion has an upper surface, a lower surface and a second transverse hole therethrough, the hole having a shape for receiving the second bone fastener, and wherein the first bone fastener is received within the first transverse hole, and the second bone fastener is received within the second transverse hole, wherein the intermediate portions are conformable and made of a braided material, and wherein the upper surface of each end portion is smooth.

Figure 4C:
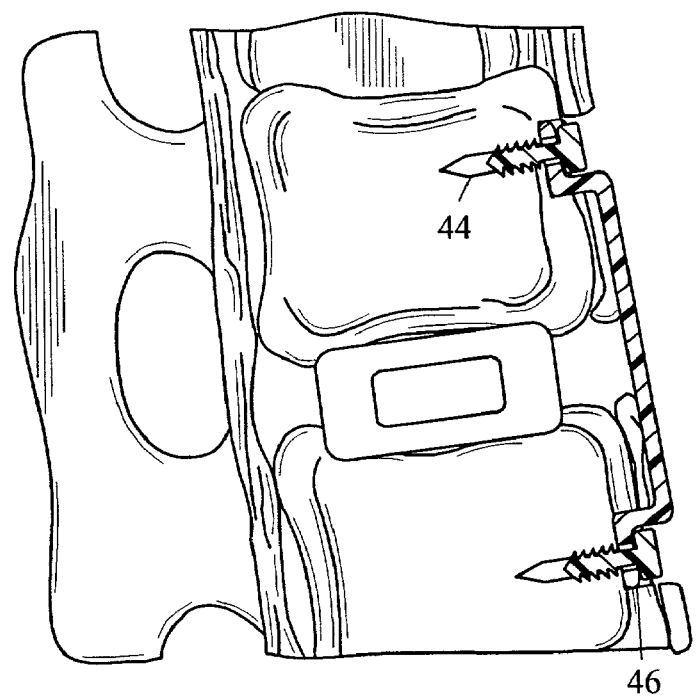
FIG. 4c presents the system of FIG. 4a attached to the spine.

Now referring to FIG. 4c, the end portion 47 of the ligament body is formed into an L-shape with transverse hole 48 therethrough to accept the bone fastener 41. The vertebral body is prepared with a first narrow but deep hole 44 for the bone fastener and a wider but shallower hole 46 for the ligament end. Once the ligament and achor are inserted, this configuration provides for a very low profile. Furthermore, this design is more amenable to using a screw-type anchor.

In some embodiments, at least the end portions of the ligament and the attachment end of the bone fastener are made of the same material. When the materials are so selected, these portions may be easily made and pre-connected in an integral fashion. This feature also eliminates the need for sutures.

Preferably, the ligament and bone fastener components are pre-connected. That is, the components are physically attached prior to their placement upon the spine. Pre-connected components are advantageous because their secured attachment to each other are guaranteed, and the surgeon need not waste time in making the attachment. Components may be pre-connected by physical locking, physical connection (as in FIG. 3 by bonding, or by making the components from the same material and integrally connecting them. When the preconnected components are integrally formed (by, for example, molding or thermoforming), there is no danger of micromotion. Therefore, in accordance with the present invention, there is provided an intervertebral connection system comprising:

a) a ligament comprising first and second end portions, and
b) first and second bone fasteners, wherein the first bone fastener is pre-connected to the first end portion of the ligament, and the second bone fastener is pre-connected to the second end portion of the ligament.

Figure 5:
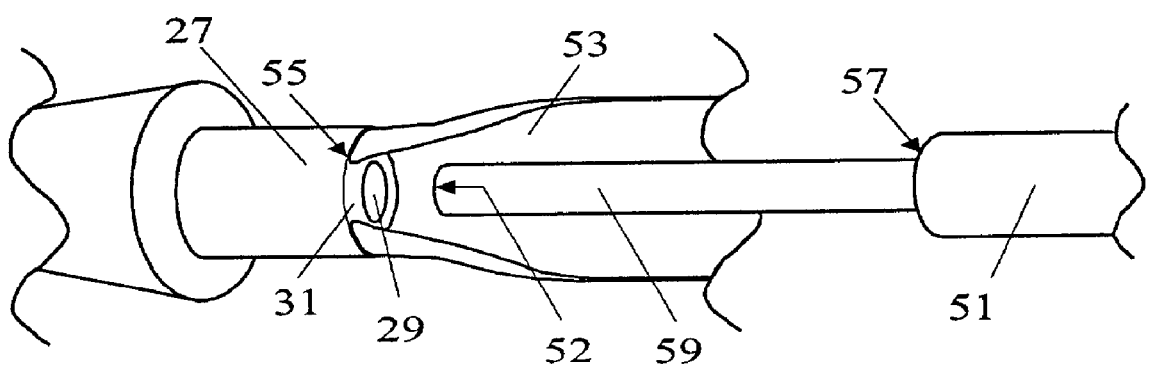
FIG. 5 presents the step of inserting each bone fastener into the recess in the anterior surfaces.

Now referring to FIG. 5, in some embodiments, the system has a port for accepting a driver 51 which drives the bone fastener into the vertebral body. In FIG. 5, the port comprises a recess 29. In some embodiments, the end portion 53 of ligament is molded to the upper surface 31 of the attachment end 27 of the anchor such that an insertion tip 59 of driver 51 can be inserted into the anchor recess 29 without damaging the ligament. FIG. 5 illustrates such an attachment wherein the end portion 53 of the ligament is attached semi-circumferentially to the outer edge 55 of the upper surface 31 of the anchor. It is appreciated that other embodiments may function similarly, such as attaching the ligament to one half face of the anchor upper surface 31 and modifying the driver shoulder to contact the other half face of the anchor surface. Furthermore, the lower surface 57 of the driver shoulder is able to contact the upper surface 31 of the bone anchor. Preferably, the lower surface 52 of the insertion tip 59 is also able to contact the bottom 30 of the anchor recess 29. With these features, the driver can be used to fully seat the anchor in the vertebral body and apply pretension to the ligament. When the diameter of recess 29 is substantially equal to the diameter of tip 59, the insertion tip will temporarily reinforce the anchor during the insertion step.

In some embodiments, the lower surface 30 of the recess is located at a depth such that both the distal end of tip 59 and shoulder 59 will respectively contact the lower surface 30 (as shown in FIG. 2c) and upper surface 31 of the recess.

The present invention is particularly useful for augmenting single or multi-level anterior interbody fusions. In some embodiments, the system is designed for use in the anterior lumbar region of the spine, and so is characterized by relatively larger ligament lengths (between 20 mm and 30 mm) in order to span the disc space. In other embodiments, the system is designed for use in the cervical region of the spine, and so is characterized by ligaments having relatively small lengths (such as between 12 mm and 15 mm) and small thickness (such as between 0.5 mm and less than 2 mm) in order to avoid exposure to the esophagus.

Generally, the bone fasteners of the present invention may be fastened to any portion of the anterior, lateral or posterior surface of the vertebral body. Preferably, however, the bone fasteners are fastened to the anterior surface in order to take advantage of the low profile produced by the system and to avoid a second surgery (posterior) in anterior interbody fusion procedures.

Therefore, there is provided a method of stabilizing a pair of vertebrae, each vertebrae having a surface, comprising the steps of:

a) providing an intervertebral connection system comprising:
  i) a ligament having first and second end portions, and
  ii) first and second bone fasteners, wherein the ligament is between the first and second bone fasteners, the first end portion of the ligament being adjacent the first bone fastener, the second end portion of the ligament being adjacent the second bone fastener, and b) fully inserting the first bone fastener and at least a portion of the first end portion of the ligament into the first vertebra to a location below the first vertebral surface, and
c) fully inserting the second bone fastener and at least a portion of the second end portion of the ligament into the second vertebra to a location below the second vertebral surface.

In addition, the ligament of the present invention may be coated or embedded with one or more biologically or pharmaceutically active compounds such as cytokines (e.g., lymphokines, chemokines, etc.), attachment factors, genes, peptides, proteins, nucleotids, carbohydrates, cells or drugs.

Regarding in particular the single-level embodiment of this invention with bone anchors integrally attached, the device is amenable for use in minimally invasive spine surgical procedures. Due to the long and slender, conformable nature of the device, it can be inserted through a relatively small incision and could potentially be used in a laparoscopic procedure. Furthermore, the single-piece aspect of the design minimizes the possibility of losing device components in the body cavity when performing the laparoscopic surgery.

In addition, it has been found that fastening the bone fasteners in close proximity to the vertical portion of the endplate portions of the vertebral bodies results in a more secure fixation of the system. Without wishing to be tied to a theory, it is believed that the relatively higher hardness of the endplate region (owing to its higher density) restricts any undesired motion of the fixed fastener. Therefore, preferably, the bone fasteners of the present invention are fastened to the superior or inferior portions of the vertebral bodies near their endplates in the transition zone between the cortical and cancellous bone regions. In some embodiments, therefore, a kit is fashioned which advantageously links a disk prosthesis component suitable as a replacement for a particular natural disk with an intervertebral connection system having a ligament whose length is designed for insertion of the bone fasteners into the endplates adjacent that natural disk. That is, there is provided a kit comprising:

a) a disk prosthesis having a height, and
b) an intervertebral connection system comprising a ligament having a length, wherein the ligament length is between 1 and 3 times the height of the disk prosthesis.

EXAMPLE I

Figure 6A:
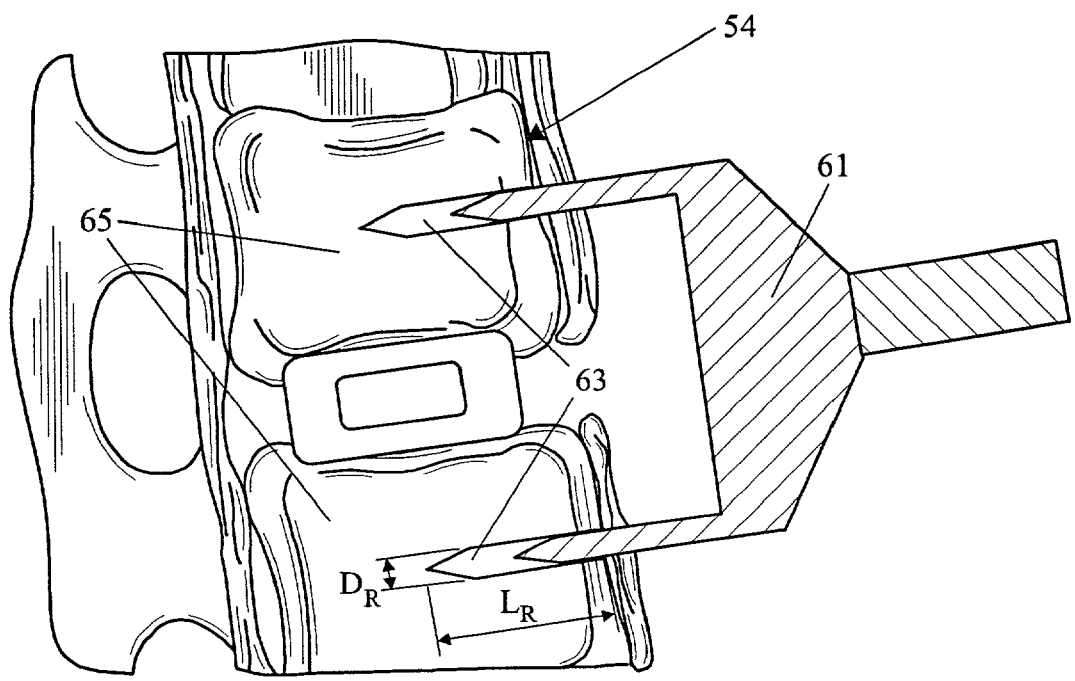
FIG. 6a presents a cross-sectional view of the step of providing a recess upon the anterior surface of each vertebrae.

Now referring to FIG. 6a, a punch 61 is used to create a pair of recesses 63 on the anterior surfaces 54 of the adjacent vertebral bodies 65. These recesses are shaped to have approximately the same diameter $D_R$ as the shank diameter of the bone fastener, and a depth $L_R$ at least as deep as the length $L_{BF}$ of the bone fastener.

Figure 6B:
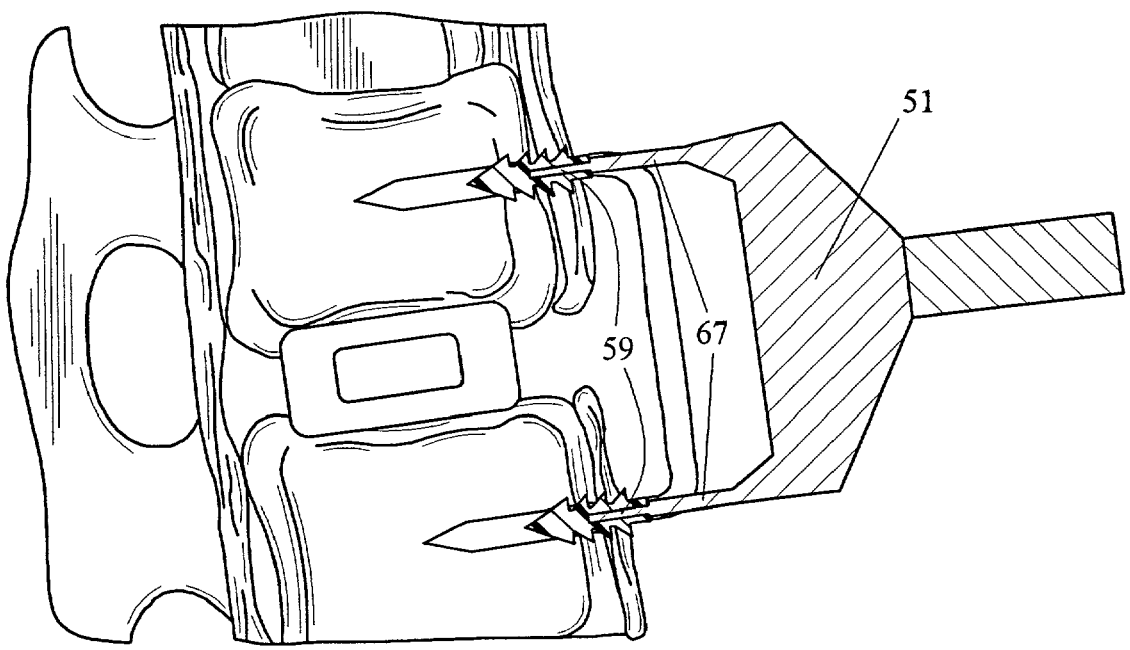
FIG. 6b presents the insertion of the system into a vertebral recess via an insertion tool.
Figure 7:
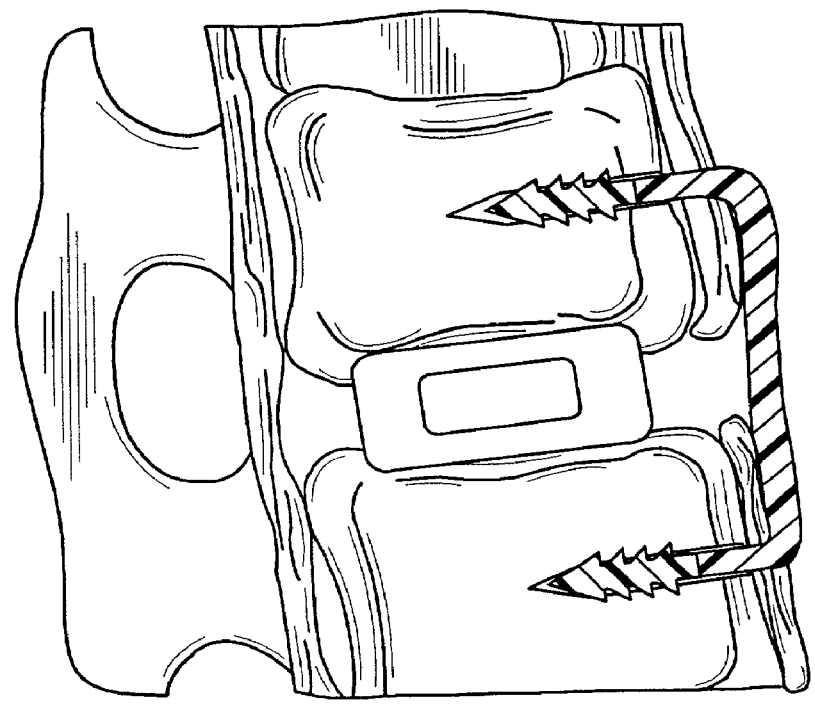
FIG. 7 presents a cross-sectional view of the fixation of adjacent vertebrae by the system of the present invention, wherein the bone fasteners are fully inserted into the recesses.
Figure 8:
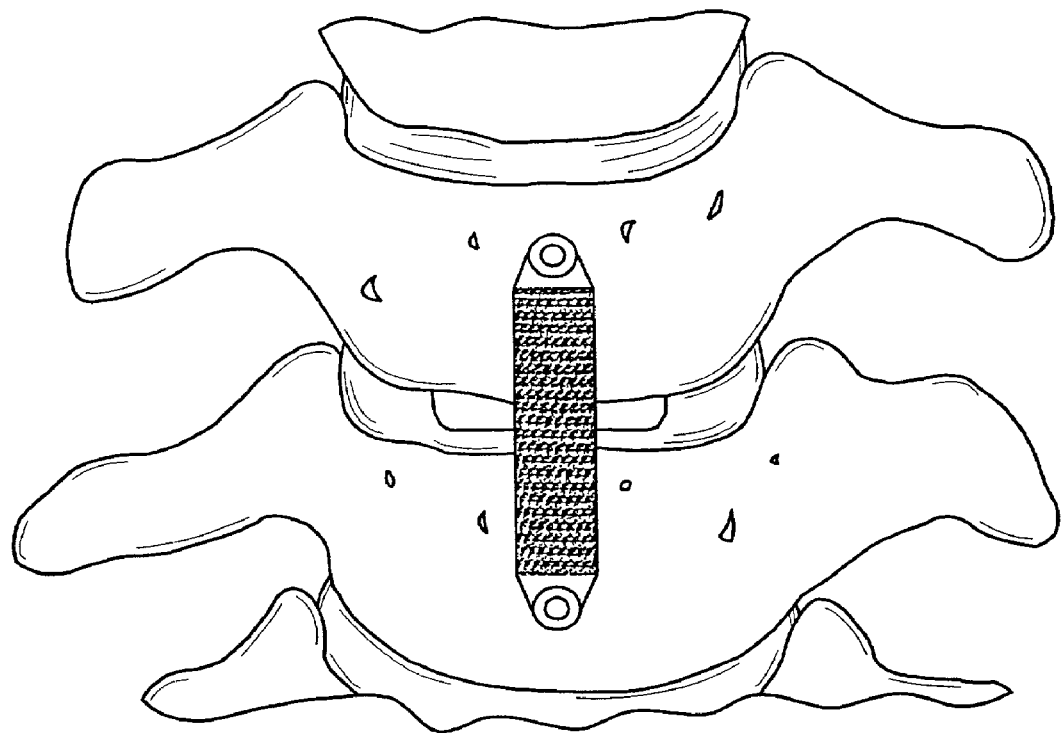
FIG. 8 presents an aerial view of FIG. 7.

As shown in FIG. 6b, the implant of FIG. 2 is affixed to the insertion tool 51 by inserting tips 59 into the implant recesses. The arms 67 are long enough to fully bury the bone fasteners in the vertebral body recesses. Therefore, this procedure requires only two steps: punching recesses in the vertebral body, and inserting the implant, thereby making it simple and rapid. This is a very attractive feature for use in spine fusion procedures which are very lengthy. Optionally, a single tip driver (not shown) may be used to further drive one bone fastener further into the vertebral body, thereby further tensioning the ligament. The completed procedure is shown in FIGS. 7 and 8.

EXAMPLE II

In this example, the implant of the present invention is applied to a two-level spine fusion procedure after discectomy and insertion of two interbody devices, as shown in FIG. 9. However, as shown in FIG. 10*b* a separate fastening element 102, such as a cannulated staple, may be used to additionally secure the woven strip at multiple locations.

Figure 13A:
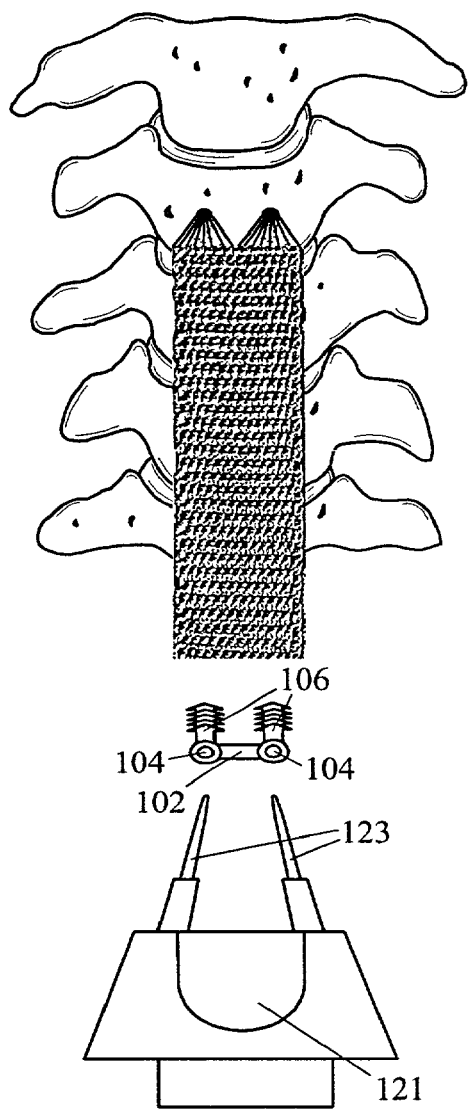
FIGS. 13a-13c present aerial views of providing an intermediate bone fastener upon the ligament of the present invention.
Figure 13B:
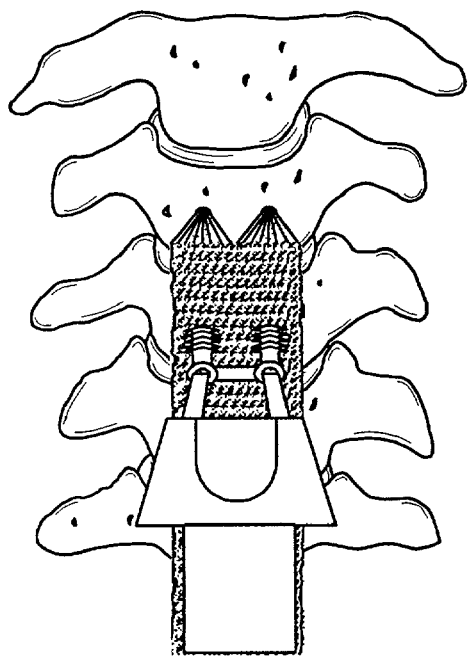
Figure 13C:
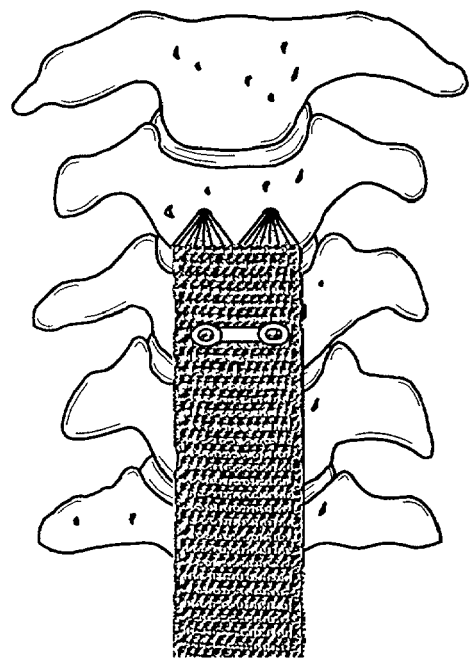
Figure 14:
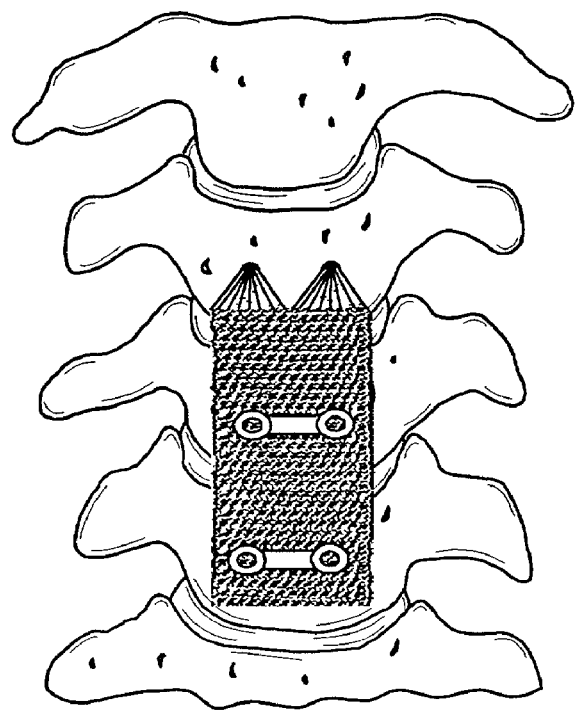
FIG. 14 present an aerial view of providing two intermediate bone fastener upon the ligament of the present invention.
Figure 15:
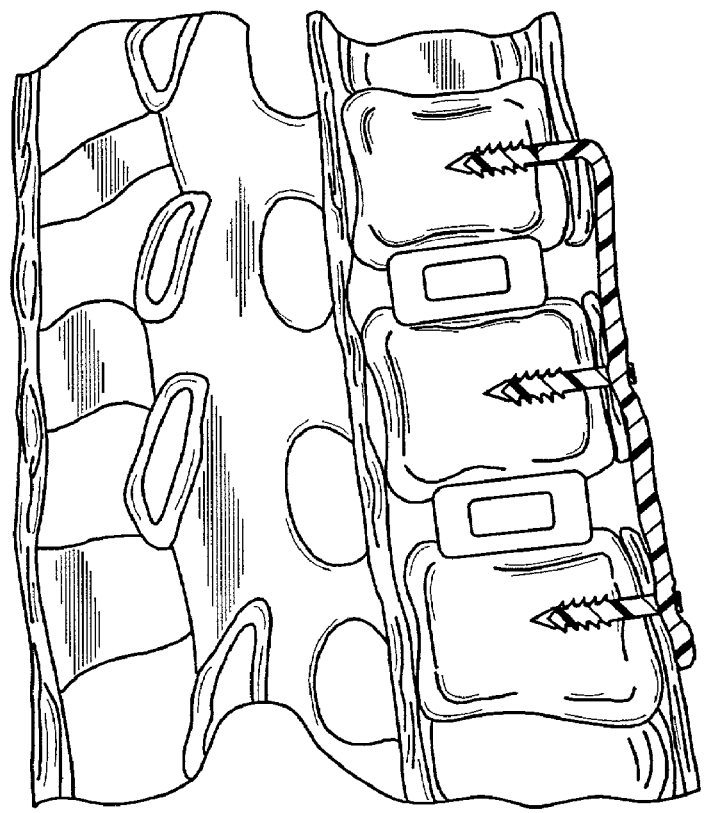
FIG. 15 presents a cross-sectional view of FIG. 14.

As shown in FIG. 10*a*, an implant 101 of the present invention comprising two bone fasteners 103 integrally attached to a single end portion 105 of the woven strip ligament 107 is provided. As shown in FIG. 11, two recesses 111 shaped to receive bone fasteners 103 are then prepared in the upper vertebral body 113 using a punch device 115. Next, as shown in FIG. 12, the implant 101 is affixed to insertion tool 121 by inserting the prong tips 123 into the cannulas 104 of the device. As shown in FIG. 15, upon insertion, the bone fasteners are buried in the vertebral body to minimize profile. Next, the adjacent vertebral body is prepared for receiving the secondary staple anchor 102 using the same punch device described in FIG. 11. The punch is inserted through the ligament body, tension is applied to the ligament, and then the holes are punched. Next, as shown in FIGS. 13*a-c*, the tips 123 of punch 121 are inserted into cannulas 104 of cannulated staple 102, appropriate tension is applied to the strip, and then the tips 106 of staple 102 are punched through the woven ligament and into the bone recesses to secure the staple. These steps are repeated until the implant has been secured to each level. The results of the completed procedure are shown in FIGS. 14 and 15.

In another embodiment, the staple 102 of FIG. 13 is replaced with a device comprising a pair of washers connected by a ligament, and bone screws pass through the washers. In this case, the bone screws ensure optimal securing of the implant.

Therefore, there is provided an intervertebral connection system comprising:
a) a ligament having:
   i) a central portion,
   ii) first and second end portions, and
   iii) first and second intermediate portions, wherein the first intermediate portion is conformable and is disposed between the central portion and the first end portion, and the second intermediate portion is disposed between the central portion and the second end portion,
b) a first shoulderless bone fastener, and
c) a shouldered bone fastener wherein the first end portion is shaped to cooperatively connect to the first shoulderless bone fastener, and the shouldered bone fastener is received through the second end portion.

EXAMPLE III

FIG. 16*a* shows the abnormal shape of a scoliotic spine in the thoracolumbar area. Prior art solutions to scoliosis are taught in PCT Patent Publication Number WO9322989 ("Campbell") and PCT Patent Publication Number WO64363 ("Drewry").

Drewry describes a spinal tether for supporting spine instability, correction of deformities and as a tension band to facilitate fusion. The tether has an eyelet on one side that is formed using a crimp and more crimps are formed at other places along the tether to secure the tether to elements of the spine, grommets or other spine devices such as screws. Drewry does not disclose a system having two bone fasteners, nor integrally connected ligaments and bone fasteners, nor is there any mention of using resorbable materials. Campbell describes a shaft, referred to as a thoracodorsal distractor that connects with metallic slings that encircle the ribs or extend to the sacrum, and the shaft can be shortened through successive adjustments to achieve correction in the thoracic spine. Campbell does not disclose a system having two bone fasteners, nor integrally connected ligaments and bone fasteners, nor is there any mention of using resorbable materials.

Accordingly, another potential use of the present invention is for correction of spinal deformities such as pediatric and adult scoliosis. By placing systems of the present invention in tension on the lateral aspect of the vertebral bodies at the convex portions of the curve, as indicated in FIGS. 16*a* and 16*b* (with or without interbody bone or fusion devices), the spine can be pulled into alignment. The device can then provide temporary stabilization to the corrected spine until fusion can be achieved. The tensionable quality of the ligaments of the present invention allows the surgeon to precisely tailor the amount of tension required to provide the desired alignment.

The invention is particularly useful as an absorbable device to provide correction for juvenile and adolescent idiopathic scoliosis. In this application, segmental correction could be achieved as described above without the use of interbody devices, since it is generally not desirable to induce arthrodesis. State-of-the-art scoliosis correction systems are rigid and permanent and must be adjusted or removed within approximately two years after initial surgery. With a bioabsorbable ligament system, the device is preferably tailored to lose strength within two years, thereby allowing the patient's spine to grow without a second surgical intervention.

For adult scoliosis, the bioabsorbable ligament is preferably used with an interbody fusion device, such as a cage, to promote arthrodesis and achieve permanent correction. Once the fusion has occurred, the device is obsolete and will disappear if the device is bioabsorbable, thus preventing long-term device-related complications which again, would require a revision surgery.

Therefore, in one preferred method of the invention, the first 101 and second 103 vertebrae form a portion of a first lateral aspect 105 of a scoliotic spine 107 having a convex curve 109, the first bone fastener 111 is inserted into the first lateral aspect 105 of the first vertebra 101 and the second bone fastener 113 is inserted into the first lateral aspect 105 of the second vertebra 103, and the insertion step of step c) tensions the ligament, thereby at least partially straightening the convex curve. This procedure may then be repeated as per FIG. 16*b* to substantially straighten the curve.

Figure 17:
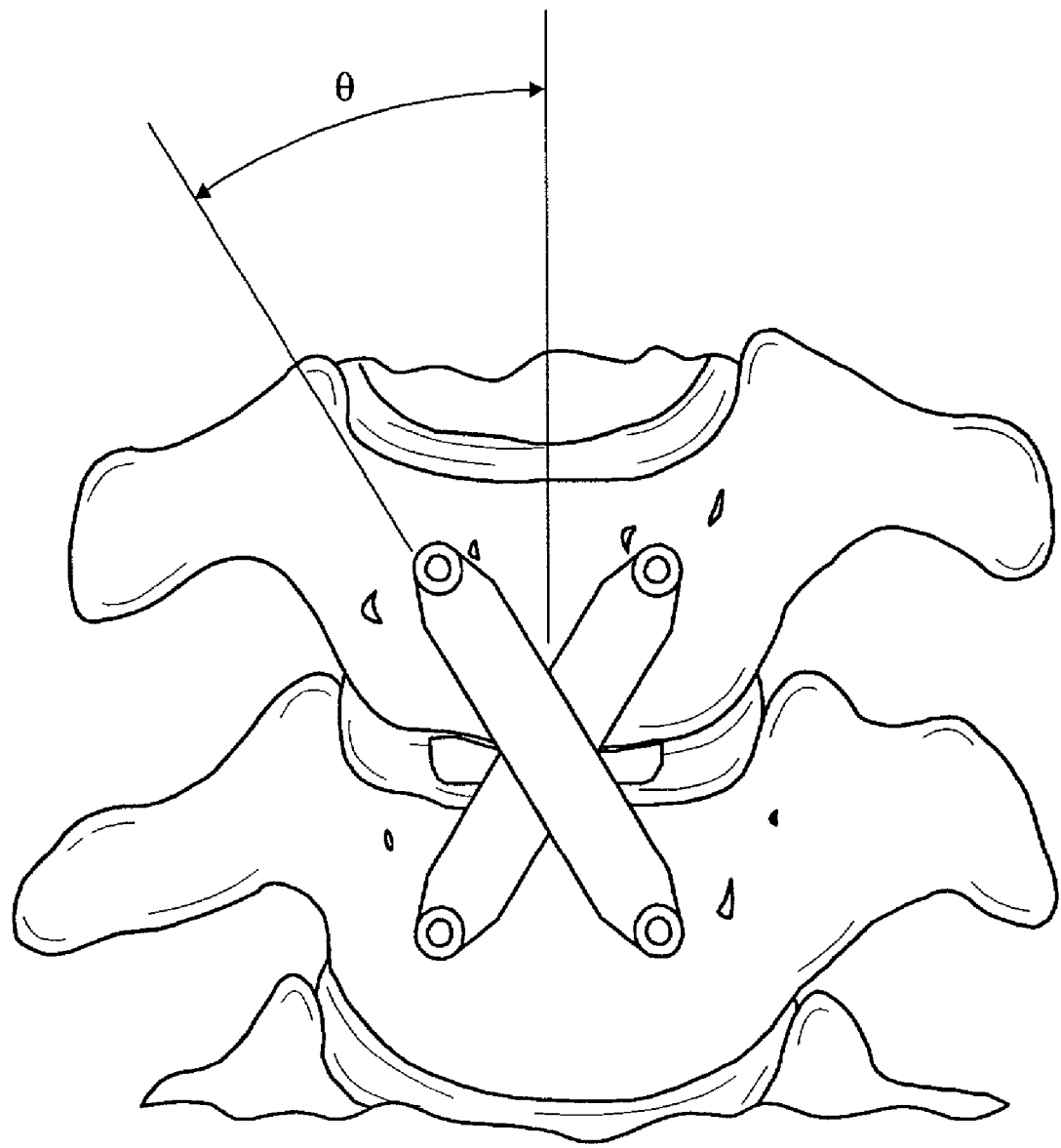
FIG. 17 presents how two systems of the present invention may be used in overlapping fashion.

Now referring to FIG. 17, in some embodiments, and particularly for cervical applications, it is desirable to apply two ligament devices to a single level procedure such that the devices are angled with respect to the spinal column and cross one another. This arrangement provides increased stability in axial rotation while maintaining adequate resistance to extension. Preferably, the angle θ is no more than 45 degrees, more preferably between 30 and 40 degrees.

This invention provides a combination implant and insertion method that is simple, allows for quick implantation and provides rigid, temporary anterior tensile support to complement an anterior interbody fusion procedure. The proposed invention would minimize the damage caused to these supporting elements, reduce surgery time, reduce time for rehabilitation, and therefore reduce greatly the cost of the treatment.

We claim:

1. An intervertebral connection system comprising:
   a) a ligament having:
      i) a central portion,
      ii) first and second end portions, and
      iii) first and second conformable portions, each conformable portion comprising a fabric,
   wherein the first conformable portion is disposed between the central portion and the first end portion, and the second conformable portion is disposed between the central portion and the second end portion, and
   b) first and second shoulderless bone fasteners,
   wherein the first end portion is shaped to cooperatively connect to the first bone fastener, and the second end portion is shaped to cooperatively connect to the second bone fastener.

2. The system of claim 1 wherein the ligament is bioresorbable.

3. The system of claim 1 wherein the bone fastener comprises an attachment end portion, wherein the attachment end portion has a shape for fitting a driver.

4. The system of claim 1 wherein each bone fastener further comprises an insertion end portion, wherein the insertion end portion is drivable.

5. The system of claim 1 wherein at least one of the central and conformable portions is tensionable.

6. The system of claim 5 wherein the tensionable portion is braided.

7. The system of claim 1 wherein the central portion is tensionable.

8. The system of claim 7 wherein the central portion and conformable portions each have a length, and the length of the central portion is at least twice as long as either conformable portion.

9. The system of claim 1 wherein at least one of the central and conformable portions is extensible.

10. The system of claim 9 wherein the extensible portion is braided.

11. The system of claim 1 Wherein the central portion is extensible.

12. The system of claim 11 wherein the central portion and conformable portions each have a length, and the length of the central portion is at least twice as long as either conformable portion.

13. An intervertebral connection system comprising:
    a) a ligament comprising first and second end portions, and
    b) first and second bone fasteners,
    wherein the first bone fastener is connected to the first end portion of the ligament, and the second bone fastener is connected to the second end portion of the ligament, and
    wherein the first bone fastener is configured to accept a driver.

14. The system of claim 13 wherein the first bone fastener has an upper surface connected to the first end portion of the ligament, and the upper surface has a recess.

15. The system of claim 14 wherein the recess houses a rescue screw.

16. The system of claim 13 wherein the upper surface has a circumference, and the second end of the ligament portion attaches to at least half of the circumference.

17. The system of claim 16 wherein at least one of the lateral protrusions defines an angle α of no more than 45 degrees.

18. The system of claim 16 wherein at least one of the lateral protrusions defines an angle α of no more than 30 degrees.

19. The system of claim 16 wherein at least one of the lateral protrusions defines an angle α of between 20 degrees and 30 degrees.

20. The system of claim 16 wherein the shank has a diameter D, and at least one of the lateral protrusions has a height H, and the height H of the lateral protrusion is no more than 70% of the diameter D of the shank.

21. The system of claim 13 wherein the upper surface has a circumference, and the second end of the ligament portion attaches to substantially the full circumference.

22. An intervertebral connection system comprising:
    a) a conformable ligament comprising first and second end portions, each end portion comprising a fabric, and
    b) first and second bone fasteners,
    wherein the first bone fastener is connected to the first end portion of the ligament, and the second bone fastener is connected to the second end portion of the ligament,
    wherein the bone fastener is made of a bioresorbable PLA/PLG copolymer and is shoulderless.

23. The system of claim 22 wherein the conformable ligament further comprises:
    i) a central portion, and
    ii) first and second conformable portions, each conformable portion comprising a fabric,
    wherein the first conformable portion is disposed between the central portion and the first end portion, and the second conformable portion is disposed between the central portion and the second end portion.

24. An intervertebral connection system comprising:
    a) a conformable ligament comprising first and second end portions, each end portion comprising a fabric, and
    b) first and second bone fasteners,
    wherein the first bone fastener is pre-connected to the first end portion of the ligament, and the second bone fastener is pre-connected to the second end portion of the ligament.

25. The system of claim 24 wherein the pre-connection is accomplished by physical locking.

26. The system of claim 24 wherein the pre-connection is accomplished by physical connection.

27. The system of claim 24 wherein the pre-connection is accomplished by integral connection.

28. An intervertebral connection system comprising:
    a) a compressible ligament comprising first and second end portions and having at least one bioresorbable portion, and
    b) first and second bone fasteners,
    wherein the first end portion is shaped to cooperatively connect to the first bone fastener, and the second end portion is shaped to cooperatively connect to the second bone fastener.

29. The system of claim 28 wherein the ligament further comprises a bioresorbable central portion.

30. The system of claim 28 wherein the ligament further comprises a central portion, and conformable portions disposed between the central portion and each end portion, wherein each conformable portion is bioresorbable.

31. The system of claim 28 wherein each end portion is bioresorbable.

32. The system of claim 28 wherein each bone fastener is bioresorbable.

33. The system of claim 28 wherein the bioresorbable portion is selected front the group consisting of a polymer and a copolymer.

34. The system of claim 28 wherein the bioresorbable portion is selected from the group consisting of PLA, PGA and copolymers of PLA and PGA.

35. The system of claim 28 wherein the bioresorbable portion is a copolymer comprising PLA and PGA.

36. The system of claim 35 wherein the copolymer comprises between 70 wt % and 99 wt % PLA, and 1 wt % and 30 wt % PGA.

37. An intervertebral connection system comprising:
 a) a compressible ligament comprising first and second end portions, and
 b) first and second bone fasteners,
 wherein each bone fastener and the ligament are bioresorbable.

38. The system of claim 37 wherein the ligament and each bone fastener has a resorption time, and wherein the resorption time of the ligament is less than that of each bone fastener.

39. The system of claim 37 wherein the ligament is tensionable.

40. The system of claim 37 wherein the bioresorbable ligament is selected from the group consisting of a polymer and a copolymer.

41. The system of claim 37 wherein the bioresorbable ligament is selected from the group consisting of PLA, PGA and copolymers of PLA and PGA.

42. An intervertebral connection system comprising:
 a) a ligament having:
  i) a central portion,
  ii) first and second end portions, and
  iii) first and second conformable portions,
 wherein the first conformable portion is disposed between the central portion and the first end portion, and the second conformable portion is disposed between the central portion and the second end portion
 b) first and second shoulderless bone fasteners,
 wherein the first end portion is connected to the first bone fastener, and the second end portion is connected to the second bone fastener, and
 wherein the central portion is made of a first material having a first resorption time, the end portion is made of a second material having a second resorption time, and the first material has a shorter resorption time than that of the second material.

43. An intervertebral connection system comprising:
 a) a compressible ligament comprising first and second end portions, and
 b) first and second bone fasteners, each bone fastener having an attachment end comprising a ceramic material and a shank comprising a polymer material.

44. An intervertebral connection system comprising:
 a) a ligament comprising first and second end portions, and
 b) first and second bone fasteners,
 wherein the first end portion is pivotally connected to the first bone fastener, and the second end portion is pivotally connected to the second bone fastener.

45. An intervertebral connection system comprising:
 a) a ligament having:
  i) a central portion,
  ii) first and second end portions, each end portion comprising a fabric, and
  iii) first and second intermediate portions,
 wherein the first intermediate portion is disposed between the central portion and the first end portion, and the second intermediate portion is disposed between the central portion and the second end portion, and
 b) first and second shoulderless bone fasteners,
 wherein the first end portion is shaped to cooperatively connect to the first bone fastener, and the second end portion is shaped to cooperatively connect to the second bone fastener, and
 wherein at least one of the central and intermediate portions is extensible.

46. The system of claim 45 wherein the extensible portion has a length which can be increased by 25% without exceeding its yield point.

47. The system of claim 45 wherein the extensible portion comprises a textile.

48. The system of claim 45 wherein the extensible portion is a braided yarn.

49. The system of claim 45 wherein the central portion is extensible.

50. The system of claim 45 wherein the central portion and end portions each have a length, and the length of the central portion is at least twice as long as either end portion.

51. An intervertebral connection system comprising:
 a) a ligament having:
  i) a central portion,
  ii) first and second end portions, and
  iii) first and second intermediate portions,
 wherein the lint intermediate portion is disposed between the central portion and the first end portion, and the second intermediate portion is disposed between the central portion and the second end portion, and
 b) first and second bone fasteners,
 wherein the first end portion has an upper surface, a lower surface and a first transverse hole therethrough, the hole having a shape for receiving the first bone fastener, and the second end portion has an upper surface, a lower surface and a second transverse hole therethrough, the hole having a shape for receiving the second bone fastener, and
 wherein the first bone fastener is received within the first transverse hole, and the second bone fastener is received within the second transverse hole,
 wherein the intermediate portions are conformable and made of a braided material, and
 wherein the upper surface of each end portion is smooth.

52. The system of claim 51 wherein the bone fastener is a screw.

53. The system of claim 51 wherein the upper surface of the first end portion is integral with the first conformable portion.

54. The system of claim 51 wherein the upper surface of the second end portion is integral with the second conformable portion.

55. An intervertebral connection system comprising:
 a) a ligament having:
  i) a central portion,
  ii) first and second end portions, and
  iii) first and second intermediate portions,
 wherein the first intermediate portion is conformable and is disposed between the central portion and the first end portion, and the second intermediate portion is disposed between the central portion and the second end portion, b) a first shoulderless bone fastener, and
c) a shouldered bone fastener,
wherein the first end portion is shaped to cooperatively connect to the first shoulderless bone fastener, and the shouldered bone fastener is received through the second end portion.

56. A method of stabilizing a pair of vertebrae, each vertebrae having a surface, comprising the steps of:
   a) providing an intervertebral connection system comprising:
      i) a ligament having first and second end portions, and
      ii) first and second bone fasteners,
      wherein the ligament is between the first and second bone fasteners, the first end portion of the ligament being adjacent the first bone fastener, the second end portion of the ligament being adjacent the second bone fastener, and
   b) fully inserting time first bone fastener and at least a portion of the first end portion of the ligament into the first vertebra to a location below the first vertebral surface, and
   c) fully inserting the second bone fastener and at least a portion of the second end portion of the ligament into the second vertebra to a location below the second vertebral surface.

57. The method of claim 56 wherein the first and second vertebrae form a portion of a first lateral aspect of a scoliotic spine having a convex curve, the first bone fastener is inserted into the first lateral aspect of the first vertebra and the second bone fastener is inserted into the first lateral aspect of the second vertebra, and the insertion step of step c) tensions the ligament, thereby at least partially straightening the convex curve.

* * * * *